US008546395B2

(12) United States Patent
Pacaud et al.

(10) Patent No.: US 8,546,395 B2
(45) Date of Patent: Oct. 1, 2013

(54) 6-CYCLOAMINO-3-(1H-PYRROLO[2,3-B] PYRIDIN-4-YL)IMIDAZO[1,2-B]PYRIDAZINE DERIVATIVES, PREPARATION THEREOF AND THERAPEUTIC USE THEREOF

(75) Inventors: Christophe Pacaud, Paris (FR); Frederic Puech, Paris (FR)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/128,998

(22) PCT Filed: Nov. 30, 2009

(86) PCT No.: PCT/FR2009/052336
§ 371 (c)(1),
(2), (4) Date: Sep. 28, 2011

(87) PCT Pub. No.: WO2010/063929
PCT Pub. Date: Jun. 10, 2010

(65) Prior Publication Data
US 2012/0010208 A1    Jan. 12, 2012

(30) Foreign Application Priority Data
Dec. 1, 2008  (FR) .................................... 08 06723

(51) Int. Cl.
*A01N 43/58* (2006.01)
*A61K 31/50* (2006.01)
*C07D 487/00* (2006.01)

(52) U.S. Cl.
USPC .......................................... 514/250; 544/236

(58) Field of Classification Search
USPC ........................................ 544/236; 514/250
See application file for complete search history.

(56) References Cited

FOREIGN PATENT DOCUMENTS

| WO | WO 2007/025540 A2 | 3/2007 |
| WO | WO 2008/138834 A1 | 11/2008 |
| WO | WO 2008/138889 A2 | 11/2008 |

*Primary Examiner* — Paul V. Ward
(74) *Attorney, Agent, or Firm* — Scully, Scott, Murphy & Presser, P.C.

(57) ABSTRACT

The invention relates to 6-cycloamino-3-(1H-pyrrolo[2,3-b]pyridin-4-yl)imidazo[1,2-b]pyridazine derivatives corresponding to the general formula (I) in which $R_2$ represents an aryl group optionally substituted with one or more halogen atoms or $C_{1-6}$-alkyl, $C_{1-6}$-alkyloxy, $C_{1-6}$-alkylthio, $C_{1-6}$-fluoroalkyl, $C_{1-6}$-fluoroalkyloxy and —CN groups or $R_2$ represents a group chosen from $C_{1-6}$-alkyl, $C_{1-6}$-fluoroalkyl, $C_{3-7}$-cycloalkyl or $C_{3-7}$-cycloalkyl-$C_{1-6}$-alkyl groups; A represents a $C_{1-7}$-alkylene group; B represents a $C_{1-7}$-alkylene group; L represents either a nitrogen atom optionally substituted with an $R_c$ or $R_d$ group, or a carbon atom substituted with an $R_{e1}$ group and an $R_d$ group or two $R_{e2}$ groups; the carbon atoms of A and of B being optionally substituted with one or more $R_f$ groups, which may be identical to or different from one another. Preparation process and therapeutic use.

17 Claims, No Drawings

6-CYCLOAMINO-3-(1H-PYRROLO[2,3-B]PYRIDIN-4-YL)IMIDAZO[1,2-B]PYRIDAZINE DERIVATIVES, PREPARATION THEREOF AND THERAPEUTIC USE THEREOF

The present invention relates to 6-cycloamino-3-(1H-pyrrolo[2,3-b]pyridin-4-yl)imidazo[1,2-b]pyridazine derivatives, to the preparation thereof and to the therapeutic use thereof, in the treatment or prevention of diseases involving casein kinase 1 epsilon and/or casein kinase 1 delta.

One subject of the present invention is the compounds corresponding to the general formula (I):

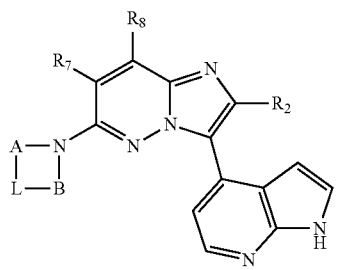

in which:
- $R_2$ represents an aryl group optionally substituted with one or more substituents chosen from halogen atoms and $C_{1-6}$-alkyl, $C_{1-6}$-alkyloxy, $C_{1-6}$-alkylthio, $C_{1-6}$-fluoroalkyl, $C_{1-6}$-fluoroalkyloxy and —CN groups or $R_2$ represents a $C_{1-6}$-alkyl, $C_{1-6}$-fluoroalkyl, $C_{3-7}$-cycloalkyl or $C_{3-7}$-cycloalkyl-$C_{1-6}$-alkyl group;
- A represents a $C_{1-7}$-alkylene group optionally substituted with one or two $R_a$ groups;
- B represents a $C_{1-7}$-alkylene group optionally substituted with an $R_b$ group;
- L represents either a nitrogen atom optionally substituted with an $R_c$ or $R_d$ group, or a carbon atom substituted with an $R_{e1}$ group and an $R_d$ group or two $R_{e2}$ groups;

the carbon atoms of A and B being optionally substituted with one or more $R_f$ groups, which may be identical to or different from one another;

$R_a$, $R_b$ and $R_c$ are defined such that:
- two $R_a$ groups may together form a $C_{1-6}$-alkylene group;
- $R_a$ and $R_b$ may together form a bond or a $C_{1-6}$-alkylene group;
- $R_a$ and $R_c$ may together form a bond or a $C_{1-6}$-alkylene group;
- $R_b$ and $R_c$ may together form a bond or a $C_{1-6}$-alkylene group;

$R_d$ represents a group chosen from a hydrogen atom and $C_{1-6}$-alkyl, $C_{3-7}$-cycloalkyl, $C_{3-7}$-cycloalkyl-$C_{1-6}$-alkyl, hydroxy-$C_{1-6}$-alkyl, $C_{1-6}$-alkyloxy-$C_{1-6}$-alkyl, $C_{1-6}$-alkylthio-$C_{1-6}$-alkyl, $C_{1-6}$-fluoroalkyl or benzyl groups;

$R_{e1}$ represents an —$NR_4R_5$ group or a cyclic monoamine optionally comprising an oxygen atom, the cyclic monoamine being optionally substituted with one or more substituents chosen from a fluorine atom and $C_{1-6}$-alkyl, $C_{1-6}$-alkyloxy and hydroxyl groups;

two $R_{e2}$ groups form, with the carbon atom that bears them, a cyclic monoamine optionally comprising an oxygen atom, the cyclic monoamine being optionally substituted with one or more $R_f$ groups, which may be identical to or different from one another;

$R_f$ represents a $C_{1-6}$-alkyl, $C_{3-7}$-cycloalkyl, $C_{3-7}$-cycloalkyl-$C_{1-6}$-alkyl, $C_{1-6}$-alkyloxy-$C_{1-6}$-alkyl, hydroxy-$C_{1-6}$-alkyl, $C_{1-6}$-fluoroalkyl, phenyl or benzyl group;

$R_4$ and $R_5$ represent, independently of one another, a hydrogen atom or a $C_{1-6}$-alkyl, $C_{3-7}$-cycloalkyl or $C_{3-7}$-cycloalkyl-$C_{1-6}$-alkyl group; and $R_7$ and $R_8$ represent, independently of one another, a hydrogen atom or a $C_{1-6}$-alkyl group.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or addition salts with acids. Such addition salts form part of the invention. These salts are advantageously prepared with pharmaceutically acceptable acids, but the salts of other acids that are useful, for example, for purifying and isolating compounds of formula (I) also form part of the invention.

The compounds of formula (I) may also exist in the form of hydrates or solvates, i.e. in the form of associations or combinations with one or more molecules of water or with a solvent. Such hydrates and solvates also form part of the invention.

In the context of the invention, the following definitions apply:

$C_{t-z}$ in which t and z may take values from 1 to 7, a carbon-based chain possibly containing from t to z carbon atoms, for example $C_{1-7}$ is a carbon-based chain that may contain from 1 to 7 carbon atoms;

alkyl, a linear or branched, saturated aliphatic group; for example, a $C_{1-7}$-alkyl group represents a linear or branched carbon-based chain of 1 to 7 carbon atoms, for example a methyl, ethyl, propyl, isopropyl, butyl, isobutyl, tert-butyl, pentyl, hexyl or heptyl;

alkylene, a linear or branched, saturated divalent alkyl group, for example a $C_{1-6}$-alkylene group represents a linear or branched divalent carbon-based chain of 1 to 6 carbon atoms, for example a methylene, ethylene, 1-methylethylene propylene or butylene;

cycloalkyl, a cyclic alkyl group, for example a $C_{3-7}$-cycloalkyl group represents a cyclic carbon-based group of 3 to 7 carbon atoms, for example a cyclopropyl, cyclobutyl, cyclopentyl, cyclohexyl or cycloheptyl;

hydroxyl, an —OH group;

—CN, a nitrile group;

cyclic monoamine, a saturated cyclic or polycyclic carbon-based chain, optionally bridged or condensed, comprising one nitrogen atom;

By way of example of a cyclic monoamine formed by N, A, L and B optionally comprising an oxygen atom, mention may in particular be made of aziridine, azetidine, pyrrolidine, piperidine, azepine, morpholine, homopiperidine, decahydroquinoline, decahydroisoquinoline, azabicycloheptane, azabicyclooctane, azabicyclononane, azaoxobicycloheptane and azaoxobicyclooctane;

hydroxyalkyl, an alkyl group in which one hydrogen atom has been substituted with a hydroxyl group;

alkyloxy, an —O-alkyl group;

alkylthio, an —S-alkyl group;

fluoroalkyl, an alkyl group in which one or more hydrogen atoms have been substituted with a fluorine atom;

fluoroalkyloxy, an alkyloxy group in which one or more hydrogen atoms have been substituted with a fluorine atom;

a halogen atom, a fluorine, chlorine, bromine or iodine atom;

aryl, a monocyclic or bicyclic aromatic group containing between 6 and 10 carbon atoms. By way of example of an aryl group, mention may be made of phenyl or naphthyl groups.

Among the compounds of general formula (I) that are subjects of the invention, a first group of compounds is constituted by the compounds for which $R_2$ represents a phenyl optionally substituted with one or more halogen atoms or $C_{1-6}$-alkyl or $C_{1-6}$-fluoroalkyl groups;
A, L, B, $R_7$ and $R_8$ being as defined above.

Among the compounds of general formula (I) that are subjects of the invention, a second group of compounds is constituted by the compounds for which $R_2$ represents a phenyl optionally substituted with one or more fluorine atoms;
A, L, B, $R_7$ and $R_8$ being as defined above.

Among the compounds of general formula (I) that are subjects of the invention, a third group of compounds is constituted by the compounds for which $R_2$ represents a 3-fluorophenyl or 4-fluorophenyl;
A, L, B, $R_7$ and $R_8$ being as defined above.

Among the compounds of general formula (I) that are subjects of the invention, a fourth group of compounds is constituted by the compounds for which $R_2$ represents a $C_{1-6}$-alkyl, $C_{1-6}$-fluoroalkyl, $C_{3-7}$-cycloalkyl or $C_{3-7}$-cycloalkyl-$C_{1-6}$-alkyl group;
A, L, B, $R_7$ and $R_8$ being as defined above.

Among the compounds of general formula (I) that are subjects of the invention, a fifth group of compounds is constituted by the compounds for which $R_2$ represents a methyl group;
A, L, B, $R_7$ and $R_8$ being as defined above.

Among the compounds of general formula (I) that are subjects of the invention, a sixth group of compounds is constituted by the compounds for which $R_7$ and $R_8$ represent, independently of each other, a hydrogen atom or a methyl group;
A, L, B, and $R_2$ being as defined above.

Among the compounds of general formula (I) that are subjects of the invention, a seventh group of compounds is constituted by the compounds for which:
A represents a $C_{1-7}$-alkylene group optionally substituted with one or two $R_a$ groups;
B represents a $C_{1-7}$-alkylene group optionally substituted with an $R_b$ group;
L represents a nitrogen atom optionally substituted with an $R_c$ or $R_d$ group;
the carbon atoms of A and of B being optionally substituted with one or more $R_f$ groups, which may be identical to or different from each other;
two $R_a$ groups may together form a $C_{1-6}$-alkylene group;
$R_a$ and $R_b$ may together form a bond or a $C_{1-6}$-alkylene group;
$R_a$ and $R_c$ may together form a bond or a $C_{1-6}$-alkylene group;
$R_b$ and $R_c$ may together form a bond or a $C_{1-6}$-alkylene group;
$R_d$ represents a group chosen from a hydrogen atom and $C_{1-6}$-alkyl, $C_{3-7}$-cycloalkyl, $C_{3-7}$-cycloalkyl-$C_{1-6}$-alkyl, hydroxy-$C_{1-6}$-alkyl, $C_{1-6}$-alkyloxy-$C_{1-6}$-alkyl, $C_{1-6}$-alkylthio-$C_{1-6}$-alkyl, $C_{1-6}$-fluoroalkyl or benzyl groups; and
$R_f$ represents a $C_{1-6}$-alkyl, $C_{3-7}$-cycloalkyl, $C_{3-7}$-cycloalkyl-$C_{1-6}$-alkyl, $C_{1-6}$-alkyloxy-$C_{1-6}$-alkyl, hydroxy-$C_{1-6}$-alkyl, $C_{1-6}$-fluoroalkyl or phenyl group;
$R_a$, $R_b$, $R_c$, $R_2$, $R_7$ and $R_8$ being as defined above.

Among the compounds of general formula (I) that are subjects of the invention, an eighth group of compounds is constituted by the compounds for which:
the cyclic amine formed by —N-A-L-B— represents a piperazinyl, diazabicycloheptyl, hexahydropyrrolopyrrolyl or octahydropyrrolopyridinyl group optionally substituted with one or more methyl, isopropyl, butylene, phenyl, benzyl, hydroxymethyl, hydroxyethyl, hydroxypropyl, hydroxymethylpropyl or hydroxymethylbutyl groups;
$R_2$, $R_7$ and $R_8$ being as defined above.

Among the compounds of general formula (I) that are subjects of the invention, a ninth group of compounds is constituted by the compounds for which:
the cyclic amine formed by —N-A-L-B— represents an (R)-3-methylpiperazin-1-yl, 3,3-dimethylpiperazin-1-yl, (cis)-3,5-dimethylpiperazin-1-yl, 4-isopropylpiperazin-1-yl, 6,9-diazaspiro[4.5]dec-9-yl, 3-phenylpiperazin-1-yl, 4-benzylpiperazin-1-yl, 3-hydroxymethylpiperazin-1-yl, 4-(2-hydroxyethyl)piperazin-1-yl, (R)-4-(2-hydroxypropyl)piperazin-1-yl, (S)-4-(2-hydroxypropyl)piperazin-1-yl, 4-(1-hydroxy-2-methylpropan-2-yl)piperazin-1-yl, 4-(2-hydroxy-2-methylpropyl)piperazin-1-yl, 4-(3-hydroxy-3-methylbutyl)piperazin-1-yl, (R)-3-phenylpiperazin-1-yl, (S)-3-phenylpiperazin-1-yl, 4-benzylpiperazin-1-yl, (cis)-5-methylhexahydropyrrolo[3,4-c]pyrrol-2(1H)-yl, (cis)-5-(2-hydroxyethyl)hexahydropyrrolo[3,4-c]pyrrol-2(1H)-yl, (4aR,7aR)-1-methyloctahydro-6H-pyrrolo[3,4-b]pyridin-6-yl, (4aS,7aS)-1-methyloctahydro-6H-pyrrolo[3,4-b]pyridin-6-yl, or (1S,4S)-5-methyl-2,5-diaza-bicyclo[2.2.1]hept-2-yl group;
$R_2$, $R_7$ and $R_8$ being as defined above.

Among the compounds of general formula (I) that are subjects of the invention, a tenth group of compounds is constituted by the compounds for which:
A represents a $C_{1-7}$-alkylene group optionally substituted with one or two $R_a$ groups;
B represents a $C_{1-7}$-alkylene group optionally substituted with an $R_b$ group;
L represents a carbon atom optionally substituted with two $R_{e2}$ groups;
the carbon atoms of A and of B being optionally substituted with one or more $R_f$ groups, which may be identical to or different from each other;
two $R_{e2}$ groups form, with the carbon atom that bears them, a cyclic monoamine optionally comprising an oxygen atom, this cyclic monoamine being optionally substituted with one or more $R_f$ groups, which may be identical to or different from one another; and
$R_f$ represents a $C_{1-6}$-alkyl group;
$R_a$, $R_b$, $R_2$, $R_7$ and $R_8$ being as defined above.

Among the compounds of general formula (I) that are subjects of the invention, an eleventh group of compounds is constituted by the compounds for which:
the cyclic amine formed by —N-A-L-B— represents a diazaspiroundecyl group;
$R_2$, $R_7$ and $R_8$ being as defined above.

Among the compounds of general formula (I) that are subjects of the invention, a twelfth group of compounds is constituted by the compounds for which:
the cyclic amine formed by —N-A-L-B— represents a 2,9-diazaspiro[5.5]undec-9-yl group;
$R_2$, $R_7$ and $R_8$ being as defined above.

Among the compounds of general formula (I) that are subjects of the invention, a thirteenth group of compounds is constituted by the compounds for which:

A represents a $C_{1-7}$-alkylene group;
B represents a $C_{1-7}$-alkylene group;
L represents a carbon atom substituted with an $R_{e1}$ group and an $R_d$ group;
$R_d$ represents a hydrogen atom;
$R_{e1}$ represents an —$NR_4R_5$ group or a cyclic monoamine optionally comprising an oxygen atom, the cyclic monoamine being optionally substituted with one or more $R_f$ groups, which may be identical to or different from one another; and
$R_f$ represents a $C_{1-6}$-alkyl, $C_{3-7}$-cycloalkyl or $C_{3-7}$-cycloalkyl-$C_{1-6}$-alkyl group;
$R_2$, $R_7$ and $R_8$ being as defined above.

Among the compounds of general formula (I) that are subjects of the invention, a fourteenth group of compounds is constituted by the compounds for which;
A represents a —$C_2H_4$— group;
B represents a —$C_2H_4$— group;
L represents a carbon atom substituted with an $R_{e1}$ group and an $R_d$ group;
$R_d$ represents a hydrogen atom; and
$R_{e1}$ represents a pyrrolidinyl group;
$R_2$, $R_7$ and $R_8$ being as defined above.

Among the compounds of general formula (I) that are subjects of the invention, a fifteenth group of compounds is constituted by the compounds for which:
the cyclic amine formed by —N-A-L-B— represents a 4-(pyrrolidin-1-yl)piperidin-1-yl;
$R_2$, $R_7$ and $R_8$ being as defined above.

Among the compounds of general formula (I) that are subjects of the invention, a sixteenth group of compounds is constituted by the compounds for which:
$R_2$ represents a methyl group;
the cyclic amine formed by —N-A-L-B— represents a (3R)-3-methylpiperazin-1-yl, 3,3-dimethylpiperazin-1-yl, (cis)-3,5-dimethylpiperazin-1-yl, 4-isopropylpiperazin-1-yl or (cis)-5-methylhexahydropyrrolo[3,4-c]pyrrol-2(1H)-yl group; and
$R_7$ and $R_8$ represent a hydrogen atom.

Among the compounds of general formula (I) that are subjects of the invention, a seventeenth group of compounds is constituted by the compounds for which:
$R_2$ represents a 3-fluorophenyl or a 4-fluorophenyl group;
the cyclic amine formed by —N-A-L-B— represents an (R)-3-methylpiperazin-1-yl, 3,3-dimethylpiperazin-1-yl, (cis)-3,5-dimethylpiperazin-1-yl, 4-isopropylpiperazin-1-yl, 6,9-diazaspiro[4.5]dec-9-yl, 3-phenylpiperazin-1-yl, 4-benzylpiperazin-1-yl, 3-hydroxymethylpiperazin-1-yl, 4-(2-hydroxyethyl)piperazin-1-yl, (R)-4-(2-hydroxypropyl)piperazin-1-yl, (S)-4-(2-hydroxypropyl)piperazin-1-yl, 4-(1-hydroxy-2-methylpropan-2-yl)piperazin-1-yl, 4-(2-hydroxy-2-methylpropyl)piperazin-1-yl, 4-(3-hydroxy-3-methylbutyl)piperazin-1-yl, (R)-3-phenylpiperazin-1-yl, (S)-3-phenylpiperazin-1-yl, 4-benzylpiperazin-1-yl, (cis)-5-methylhexahydropyrrolo[3,4-c]pyrrol-2(1H)-yl, (cis)-5-(2-hydroxyethyl)hexahydropyrrolo[3,4-c]pyrrol-2(1H)-yl, (4aR,7aR)-1-methyloctahydro-6H-pyrrolo[3,4-b]pyridin-6-yl, (4aS,7aS)-1-methyloctahydro-6H-pyrrolo[3,4-b]pyridin-6-yl, or (1S,4S)-5-methyl-2,5-diaza-bicyclo[2.2.1]hept-2-yl group; and
$R_7$ and $R_8$ represent, independently of each other, a hydrogen atom or a methyl group.

Among the compounds of general formula (I) that are subjects of the invention, an eighteenth group of compounds is constituted by the compounds for which:

$R_2$ represents a 4-fluorophenyl group;
the cyclic amine formed by —N-A-L-B— represents a 2,9-diazaspiro[5.5]undec-9-yl group; and
$R_7$ and $R_8$ represent a hydrogen atom.

Among the compounds of general formula (I) that are subjects of the invention, a nineteenth group of compounds is constituted by the compounds for which:
$R_2$ represents a 4-fluorophenyl group;
the cyclic amine formed by —N-A-L-B— represents a 4-(pyrrolidin-1-yl)-piperidin-1-yl group;
$R_7$ and $R_8$ represent a hydrogen atom.

Among the compounds of general formula (I) that are subjects of the invention, mention may especially be made of the following compounds:
1. 2-Methyl-6-[(R)-3-methylpiperazin-1-yl]-3-(1H-pyrrolo[2,3-b]pyridin-4-yl)imidazo[1,2-b]pyridazine;
2. 6-(3,3-Dimethylpiperazin-1-yl)-2-methyl-3-(1H-pyrrolo[2,3-b]pyridin-4-yl)imidazo[1,2-b]pyridazine and the trihydrochloride thereof;
3. 6-[(cis)-3,5-Dimethylpiperazin-1-yl]-2-methyl-3-(1H-pyrrolo[2,3-b]pyridin-4-yl)-imidazo[1,2-b]pyridazine and the trihydrochloride thereof;
4. 6-(4-Isopropylpiperazin-1-yl)-2-methyl-3-(1H-pyrrolo[2,3-b]pyridin-4-yl)imidazo[1,2-b]pyridazine and the trihydrochloride thereof;
5. 2-Methyl-6-[(cis)-5-methylhexahydropyrrolo[3,4-c]pyrrol-2(1H)-yl]-3-(1H-pyrrolo[2,3-b]pyridin-4-yl)imidazo[1,2-b]pyridazine and the trihydrochloride thereof;
6. 2-(4-Fluorophenyl)-6-[(R)-3-methylpiperazin-1-yl]-3-(1H-pyrrolo[2,3-b]pyridin-4-yl)imidazo[1,2-b]pyridazine;
7. {4-[2-(4-Fluorophenyl)-3-(1H-pyrrolo[2,3-b]pyridin-4-yl)imidazo[1,2-b]pyridazin-6-yl]piperazin-2-yl}methanol;
8. 6-(3,3-Dimethylpiperazin-1-yl)-2-(4-fluorophenyl)-3-(1H-pyrrolo[2,3-b]pyridin-4-yl)imidazo[1,2-b]pyridazine;
9. 6-(3,3-Dimethylpiperazin-1-yl)-2-(3-fluorophenyl)-8-methyl-3-(1H-pyrrolo[2,3-b]pyridin-4-yl)imidazo[1,2-b]pyridazine;
10. 6-(3,3-Dimethylpiperazin-1-yl)-2-(4-fluorophenyl)-8-methyl-3-(1H-pyrrolo[2,3-b]pyridin-4-yl)imidazo[1,2-b]pyridazine;
11. 6-[(cis)-3,5-Dimethylpiperazin-1-yl]-2-(4-fluorophenyl)-3-(1H-pyrrolo[2,3-b]pyridin-4-yl)imidazo[1,2-b]pyridazine;
12. 2-{4-[2-(3-Fluorophenyl)-8-methyl-3-(1H-pyrrolo[2,3-b]pyridin-4-yl)imidazo[1,2-b]pyridazin-6-yl]piperazin-1-yl}ethanol;
13. 2-{4-[2-(4-Fluorophenyl)-8-methyl-3-(1H-pyrrolo[2,3-b]pyridin-4-yl)imidazo[1,2-b]pyridazin-6-yl]piperazin-1-yl}ethanol;
14. 2-(4-Fluorophenyl)-6-(4-isopropylpiperazin-1-yl)-3-(1H-pyrrolo[2,3-b]pyridin-4-yl)imidazo[1,2-b]pyridazine;
15. 2-(4-Fluorophenyl)-6-(4-isopropylpiperazin-1-yl)-8-methyl-3-(1H-pyrrolo[2,3-b]pyridin-4-yl)imidazo[1,2-b]pyridazine;
16. (R)-1-{4-[2-(4-Fluorophenyl)-8-methyl-3-(1H-pyrrolo[2,3-b]pyridin-4-yl)imidazo[1,2-b]pyridazin-6-yl]piperazin-1-yl}propan-2-ol;
17. (S)-1-{4-[2-(4-Fluorophenyl)-8-methyl-3-(1H-pyrrolo[2,3-b]pyridin-4-yl)imidazo[1,2-b]pyridazin-6-yl]piperazin-1-yl}propan-2-ol;
18. 6-(6,9-Diazaspiro[4.5]dec-9-yl)-2-(4-fluorophenyl)-8-methyl-3-(1H-pyrrolo[2,3-b]pyridin-4-yl)imidazo[1,2-b]pyridazine;

19. 2-{4-[2-(4-Fluorophenyl)-3-(1H-pyrrolo[2,3-b]pyridin-4-yl)imidazo[1,2-b]pyridazin-6-yl]piperazin-1-yl}-2-methylpropan-1-ol;
20. 1-{4-[2-(4-Fluorophenyl)-3-(1H-pyrrolo[2,3-b]pyridin-4-yl)imidazo[1,2-b]pyridazin-6-yl]piperazin-1-yl}-2-methylpropan-2-ol;
21. 1-{4-[2-(3-Fluorophenyl)-8-methyl-3-(1H-pyrrolo[2,3-b]pyridin-4-yl)imidazo[1,2-b]pyridazin-6-yl]piperazin-1-yl}-2-methylpropan-2-ol;
22. 1-{4-[2-(4-Fluorophenyl)-8-methyl-3-(1H-pyrrolo[2,3-b]pyridin-4-yl)imidazo[1,2-b]pyridazin-6-yl]piperazin-1-yl}-2-methylpropan-2-ol;
23. 4-{4-[2-(4-Fluorophenyl)-3-(1H-pyrrolo[2,3-b]pyridin-4-yl)imidazo[1,2-b]pyridazin-6-yl]piperazin-1-yl}-2-methylbutan-2-ol;
24. (R)-2-(4-Fluorophenyl)-6-[3-phenylpiperazin-1-yl]-3-(1H-pyrrolo[2,3-b]pyridin-4-yl)imidazo[1,2-b]pyridazine and the trihydrochloride thereof;
25. (S)-2-(4-Fluorophenyl)-6-[3-phenylpiperazin-1-yl]-3-(1H-pyrrolo[2,3-b]pyridin-4-yl)imidazo[1,2-b]pyridazine and the trihydrochloride thereof;
26. 2-(4-Fluorophenyl)-8-methyl-6-[3-phenylpiperazin-1-yl]-3-(1H-pyrrolo[2,3-b]pyridin-4-yl)imidazo[1,2-b]pyridazine;
27. 6-(4-Benzylpiperazin-1-yl)-2-(4-fluorophenyl)-3-(1H-pyrrolo[2,3-b]pyridin-4-yl)imidazo[1,2-b]pyridazine;
28. (cis)-2-(4-Fluorophenyl)-6-(5-methylhexahydropyrrolo[3,4-c]pyrrol-2(1H)-yl)-3-(1H-pyrrolo[2,3-b]pyridin-4-yl)imidazo[1,2-b]pyridazine;
29. (cis)-2-(4-Fluorophenyl)-8-methyl-6-(5-methylhexahydropyrrolo[3,4-c]pyrrol-2(1H)-yl)-3-(1H-pyrrolo[2,3-b]pyridin-4-yl)imidazo[1,2-b]pyridazine;
30. (cis)-2-{5-[2-(4-Fluorophenyl)-3-(1H-pyrrolo[2,3-b]pyridin-4-yl)imidazo[1,2-b]pyridazin-6-yl]hexahydropyrrolo[3,4-c]pyrrol-2(1H)-yl}ethanol;
31. (cis)-2-{5-[2-(4-Fluorophenyl)-8-methyl-3-(1H-pyrrolo[2,3-b]pyridin-4-yl)imidazo[1,2-b]pyridazin-6-yl]hexahydropyrrolo[3,4-c]pyrrol-2(1H)-yl}ethanol;
32. 2-(4-Fluorophenyl)-8-methyl-6-((4aR,7aR)-1-methyloctahydro-6H-pyrrolo[3,4-b]pyridin-6-yl)-3-(1H-pyrrolo[2,3-b]pyridin-4-yl)imidazo[1,2-b]pyridazine;
33. 2-(4-Fluorophenyl)-8-methyl-6-((4aS,7aS)-1-methyloctahydro-6H-pyrrolo[3,4-b]pyridin-6-yl)-3-(1H-pyrrolo[2,3-b]pyridin-4-yl)imidazo[1,2-b]pyridazine;
34. 2-(4-Fluorophenyl)-6-((1S,4S)-5-methyl-2,5-diazabicyclo[2.2.1]hept-2-yl)-3-(1H-pyrrolo[2,3-b]pyridin-4-yl)imidazo[1,2-b]pyridazine;
35. 9-[2-(4-Fluorophenyl)-3-(1H-pyrrolo[2,3-b]pyridin-4-yl)imidazo[1,2-b]pyridazin-6-yl]-2,9-diazaspiro[5.5]undecane;
36. 2-(4-Fluorophenyl)-6-(4-pyrrolidin-1-ylpiperidin-1-yl)-3-(1H-pyrrolo[2,3-b]pyridin-4-yl)imidazo[1,2-b]pyridazine.

Another subject of the invention is a process for preparing compounds of the invention of formula (I).

In accordance with the invention, it is possible to prepare the compounds of general formula (I) according to the general process described in Scheme 1 below.

Generally, and as illustrated in Scheme 1, the 6-cycloamino-3-(1H-pyrrolo[2,3-b]pyridin-4-yl)imidazo[1,2-b]pyridazine derivatives of general formula (I) in which $R_2$, A, L, B, $R_7$ and $R_8$ are as defined above may be prepared from a (1H-pyrrolo[2,3-b]pyridin-4-yl)imidazo[1,2-b]pyridazine derivative of general formula (II), in which $R_2$, $R_7$ and $R_8$ are as defined above and $X_6$ represents a leaving group such as a halogen, by treatment using an amine of general formula (III) in which A, L and B are as defined previously. This reaction may be carried out by heating the reactants in a polar solvent such as pentanol or dimethylsulphoxide.

The (1H-pyrrolo[2,3-b]pyridin-4-yl)imidazo[1,2-b]pyridazine derivatives of general formula (II) as defined above may be obtained from derivatives of general formula (IV) in which $R_2$, $X_6$, $R_7$ and $R_8$ are as defined above and PG represents a protecting group for protecting an amine function such as a sulphonate, for example tosylate or any other group normally used for the protection of imidazole, pyrrole or indole ("Protective groups in organic chemistry", T. W. Greene and P. G. M. Wuts, $2^{nd}$ Edition, Wiley Interscience, p. 385-397). The conversion of the derivatives of general formula (IV) is then carried out via a deprotection reaction, for example by treatment using a base such as sodium hydroxide when PG represents a benzene or toluenesulphonyl group.

SCHEME 1

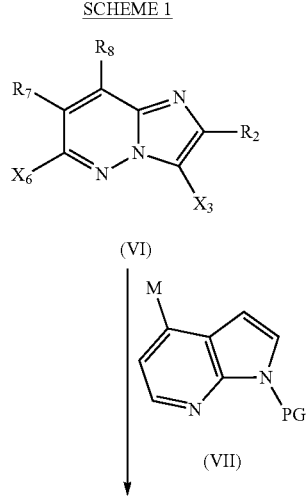

(VI)

(VII)

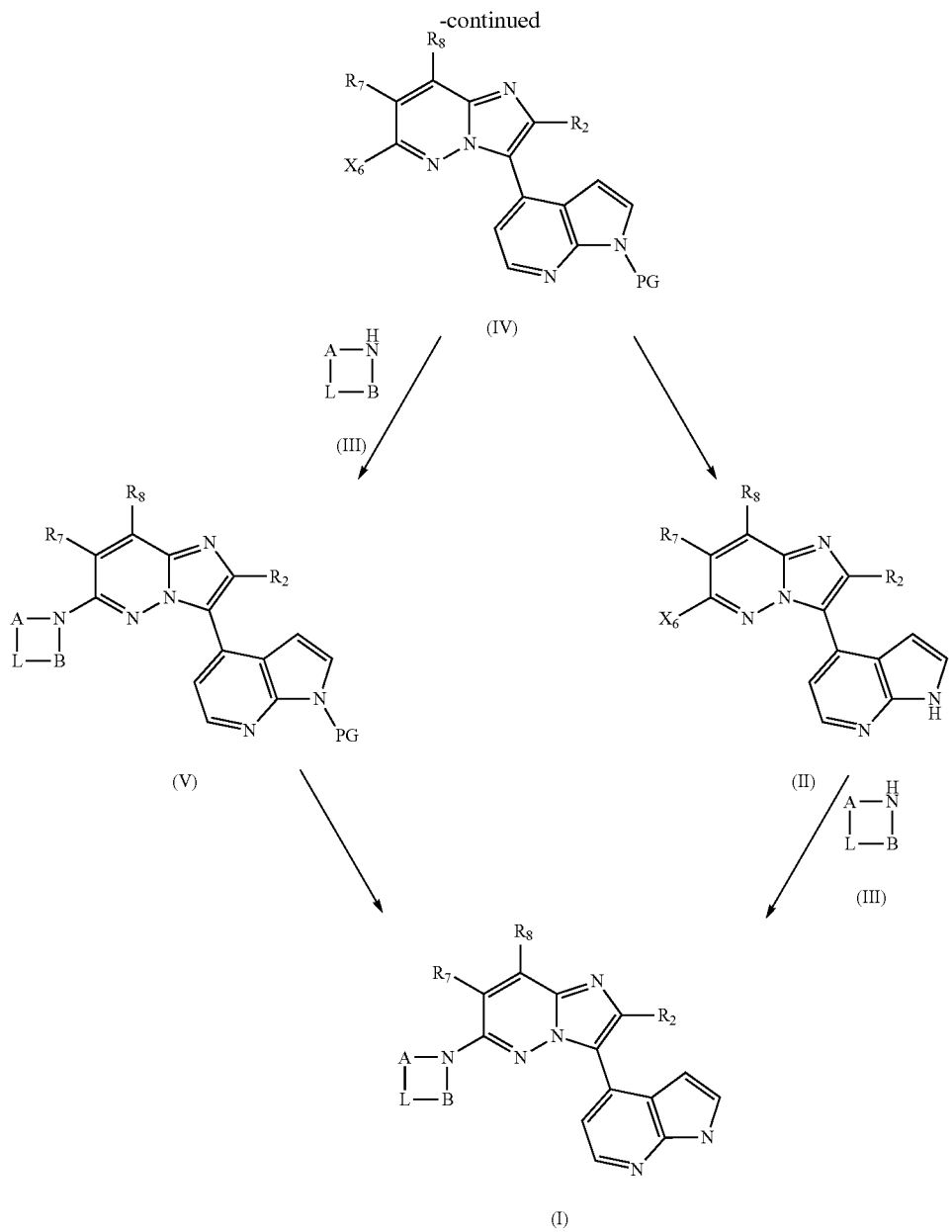

Alternatively, the 6-cycloamino-3-(1H-pyrrolo[2,3-b]pyridin-4-yl)imidazo[1,2-b]pyridazine derivatives of general formula (I) may also be prepared by deprotecting a (1H-1-pyrrolo[2,3-b]pyridin-4-yl)imidazo[1,2-b]pyridazine derivative of general formula (V) in which $R_2$, A, L, B, $R_7$, $R_8$ and PG are as defined above. The conversion of the derivatives of general formula (V) is then carried out via a deprotection reaction, for example by treatment using a base such as sodium hydroxide when PG represents a benzene or toluenesulphonyl group.

The derivatives of general formula (V) may be prepared from derivatives of general formula (IV) as defined above by treatment using an amine of general formula (III) in which A, L and B are as defined previously. This reaction may be carried out by heating the reactants in a polar solvent such as pentanol or dimethylsulphoxide.

The (1H-pyrrolo[2,3-b]pyridin-4-yl)imidazo[1,2-b]pyridazine derivatives of general formula (IV), in which $R_2$, $X_6$, $R_7$, $R_8$ and PG are as defined above, may be prepared by metal-catalysed coupling according to Suzuki conditions between a 3-haloimidazo[1,2-b]pyridazine derivative of general formula (VI) in which $R_2$, $X_6$, $R_7$ and $R_8$ are as defined above whilst $X_3$ represents a bromine or iodine atom and a 1H-pyrrolo[2,3-b]pyridine derivative of general formula (VII) in which PG is as defined above and M represents a dihydroxyboryl or dialkyloxyboryl group, most often a 4,4,5,5-tetramethyl-1,3,3,2-dioxaborolan-2-yl group.

The couplings according to the Suzuki method are, for example, carried out by heating in the presence of a catalyst such as [1,1'-bis(diphenylphosphino)ferrocene]dichloropalladium and of a mineral base such as caesium carbonate, in a mixture of solvents such as dioxane and water.

The 3-halo-(1H-pyrrolo[2,3-b]pyridin-4-yl)imidazo[1,2-b]pyridazine derivatives of general formula (VI) and the 1H-pyrrolo[2,3-b]pyridine derivatives of general formula (VII) as defined above are known or may be prepared according to methods known to a person skilled in the art.

In certain cases, the 6-cycloamino-3-(1H-pyrrolo[2,3-b]pyridin-4-yl)imidazo[1,2-b]pyridazine derivatives of general formula (I) for which the amine formed by N, L, A and B comprises a second secondary or tertiary amine may be prepared respectively from the corresponding primary or secondary amine by alkylation or reductive amination according to methods customary for a person skilled in the art.

Protecting Groups

In certain cases, the derivatives of general formulae (I) or (V) as defined above with an N-A-L-B group comprising a primary or secondary amine function, may be protected during the synthesis at this primary or secondary amine function by a protecting group, for example a benzyl or a t-butyloxycarbonyl.

The products of general structure (I) as defined above are then obtained according to the processes described, after a supplementary step of deprotection of the protecting group according to the usual conditions known to the person skilled in the art.

Leaving Groups

In the foregoing, the expression "leaving group" is understood to mean a group which may be easily cleaved from a molecule by breaking a heterolysis bond, with the departure of a pair of electrons. This group may, for example, thus be readily replaced with another group during a substitution reaction. Such leaving groups are, for example, halogens or an activated hydroxyl group such as a mesyl, tosyl, triflate, acetyl, etc. Examples of leaving groups and also references for the preparation thereof are given in "Advances in Organic Chemistry", J. March, $3^{rd}$ Edition, Wiley Interscience, p. 310-316.

The following examples describe the preparation of certain compounds in accordance with the invention. These examples are not limiting and serve only to illustrate the invention. The numbers of the compounds exemplified refer to those given in Table 1, hereinafter, which illustrates the chemical structures and the physical properties, respectively, of a number of compounds according to the invention.

EXAMPLE 1

Compound No. 29

(Cis)-2-(4-fluorophenyl)-8-methyl-6-(5-methyl-hexahydropyrrolo[3,4-c]pyrrol-2(1H)-yl)-3-(1H-pyrrolo[2,3-b]pyridin-4-yl)imidazo[1,2-b]pyridazine

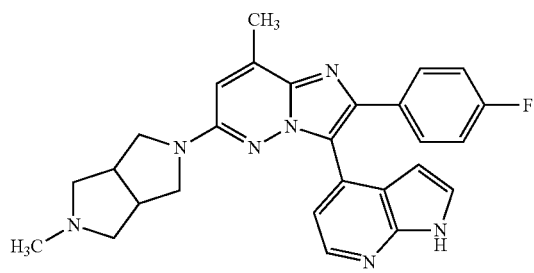 [SMILES: Cc1cc(N2CC3CN(C)CC3C2)nn2c(-c3ccnc4[nH]ccc34)c(-c3ccc(F)cc3)nc12]

Step 1.1 6-Chloro-4-methylpyridazin-3-ylamine and 6-chloro-5-methylpyridazin-3-ylamine

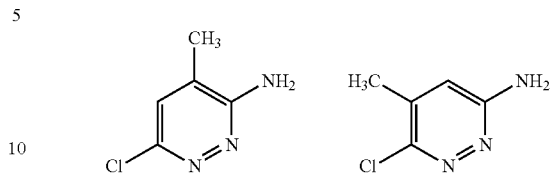

A mixture of 50.0 g (307 mmol) of 3,6-dichloro-4-methylpyridazine in 170 ml of aqueous ammonia (30%) is heated at 120° C. for 16 h in a steel reactor at an internal pressure of 10 bar.

The reactor is cooled and the reaction mixture is poured into 200 ml of water. The solid formed is isolated by filtration and dried under vacuum to give 38.7 g of a mixture containing around 45% of 6-chloro-4-methylpyridazin-3-ylamine (CAS 64068-00-4) and 55% of 6-chloro-5-methylpyridazin-3-ylamine (CAS 66346-87-0).

$^1$H NMR (CDCl$_3$) δ: 7.20 and 6.75 (2 s, 1H); (d, 0.55H); 4.9 (sl, 2H); 2.40 and 2.25 (2 s, 3H) ppm.

Step 1.2 6-Chloro-2-(4-fluorophenyl)-8-methylimidazo[1,2-b]pyridazine and 6-chloro-2-(4-fluorophenyl)-7-methylimidazo[1,2-b]pyridazine

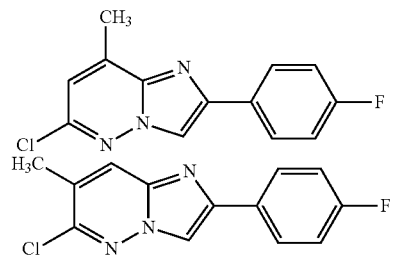

The mixture of 76 g (350 mmol) of 2-bromo-1-(4-fluorophenyl)ethanone (CAS 403-29-2) with 38.7 g (269 mmol) of the mixture of 6-chloro-4-methylpyridazin-3-ylamine and of 6-chloro-5-methylpyridazin-3-ylamine obtained in step 1.1 in 500 ml of n-butanol is heated at 120° C. for 18 hours.

The solvent is removed by evaporation under reduced pressure and the solid is triturated in acetone. After chilling, the solid is separated by filtration. The filtrate is concentrated under reduced pressure and the residue is triturated in diethyl ether. After chilling, the solvent is again separated by filtration. The two batches of solid (75 g) are combined and dissolved in 1 l of water. The solution is basified by addition of aqueous ammonia and the product is extracted with chloroform. The organic phase is dried over sodium sulphate and the solvent is evaporated under reduced pressure to give a red-brown solid. The separation of the two isomers is carried out by chromatography on a silica gel column (2×800 g) by eluting with dichloromethane. 21.9 g of 6-chloro-2-(4-fluorophenyl)-8-methylimidazo[1,2-b]pyridazine are obtained in the form of a beige solid after trituration in isopropyl ether, chilling, filtration and drying.

MP: 210-212° C.

$^1$H NMR (CDCl$_3$) δ: 8.20 (s, 1H); 8.00 (dd, 2H); 7.25 (pt, 2H); 6.95 (s, 1H); 2.75 (s, 3H) ppm.

Continuing the elution with a mixture of 2% methanol in dichloromethane gives 22.0 g of 6-chloro-2-(4-fluorophenyl)-7-methylimidazo[1,2-b]pyridazine in the form of a beige solid after trituration in isopropyl ether, chilling, filtration and drying.

MP: 196-198° C.

$^1$H NMR (CDCl$_3$) δ: 8.15 (s, 1H); 8.00 (dd, 2H); 7.80 (s, 1H); 7.20 (pt, 2H); 2.55 (s, 3H) ppm.

Step 1.3 6-Chloro-2-(4-fluorophenyl)-3-iodo-8-methylimidazo[1,2-b]pyridazine

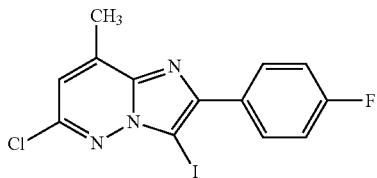 [SMILES: Cc1cc(Cl)nn2c(I)c(-c3ccc(F)cc3)nc12]

Added to a suspension of 21.9 g (83.7 mmol) of 6-chloro-2-(4-fluorophenyl)-8-methyl-imidazo[1,2-b]pyridazine in 500 ml of chloroform are 20.4 g (126 mmol) of iodine monochloride in solution in 40 to 50 ml of methanol. After stirring for 2 hours at ambient temperature, 5.0 g (31 mmol) of iodine monochloride in solution in around 10 ml of methanol are again added.

After stirring for a further 2 hours, the solution is poured over 500 ml of an aqueous solution of sodium hydrogen carbonate and the mixture is treated, with vigorous stirring, with sodium thiosulphate which is added in portions until the mixture is decoloured (red to yellow).

The organic phase is separated, dried over sodium sulphate and the solvent removed by evaporation under reduced pressure. The solid obtained is then triturated in acetonitrile, the suspension is chilled and the solid is isolated by filtration to give 30.7 g of 6-chloro-2-(4-fluorophenyl)-3-iodo-8-methylimidazo[1,2-b]pyridazine in the form of a beige powder.

MP: 190-192° C.

$^1$H NMR (CDCl$_3$) δ: 8.05 (dd, 2H); 7.10 (pt, 2H); 6.90 (5, 1H); 2.65 (s, 3H) ppm.

Step 1.4 6-Chloro-2-(4-fluorophenyl)-8-methyl-3-[1-(phenylsulphonyl)-1H-pyrrolo[2,3-b]pyridin-4-yl]imidazo[1,2-b]pyridazine

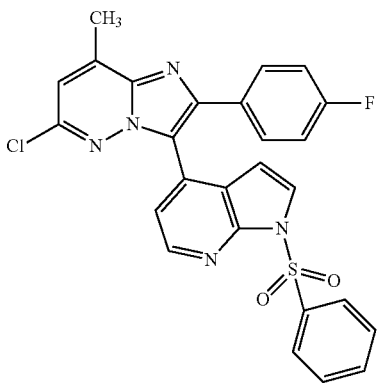 [SMILES: Cc1cc(Cl)nn2c(-c3ccnc4c3ccn4S(=O)(=O)c3ccccc3)c(-c3ccc(F)cc3)nc12]

Added to a mixture, which has been previously degassed and is under argon, of 5.00 g (12.9 mmol) of 6-chloro-2-(4-fluorophenyl)-3-iodo-8-methylimidazo[1,2-b]pyridazine, 5.95 g (15.5 mmol) of 1-(phenylsulphonyl)-4-(4,4,5,5-tetramethyl-1,3,2-dioxaborolan-2-yl)-1H-pyrrolo[2,3-b]pyridine (CAS 942919-24-6) and 12.6 g (38.7 mmol) of caesium carbonate in 50 ml of a mixture of tetrahydrofuran and water (9/1) are 0.95 g (1.2 mmol) of a complex of [1,1'-bis(diphenylphosphino)ferrocene]palladium(II) and dichloromethane.

The mixture is heated under reflux for 18 hours, then poured over 300 ml of water. The product is extracted with dichloromethane. The organic phase is separated, dried over sodium sulphate and the solvent is removed by evaporation under reduced pressure. The chestnut brown solid obtained is then chromatographed over a silica gel column (200 g) by eluting with a mixture of dichloromethane, methanol and aqueous ammonia (97/3/0.3) in order to give 5.99 g of 6-chloro-2-(4-fluorophenyl)-8-methyl-3-[1-(phenylsulphonyl)-1H-pyrrolo[2,3-b]pyridin-4-yl]imidazo[1,2-b]pyridazine in the form of a yellow powder after trituration in isopropyl ether, chilling, filtration and drying.

MP: 226-228° C.

$^1$H NMR (CDCl$_3$): δ: 8.65 (d, 1H); 8.30 (d, 2H); 7.6 (m, 7H); 7.05 (m, 3H); 6.10 (d, 1H); 2.80 (s, 3H) ppm.

Step 1.5 6-Chloro-2-(4-fluorophenyl)-8-methyl-3-(1H-pyrrolo[2,3-b]pyridin-4-yl)imidazo[1,2-b]pyridazine

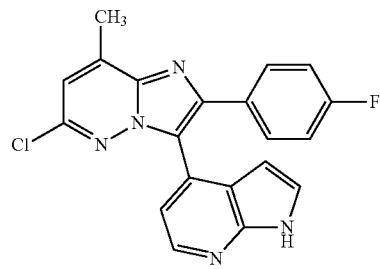 [SMILES: Cc1cc(Cl)nn2c(-c3ccnc4[nH]ccc34)c(-c3ccc(F)cc3)nc12]

Added to a suspension of 0.50 g (0.97 mmol) of 6-chloro-2-(4-fluorophenyl)-8-methyl-3-[1-(phenylsulphonyl)-1H-pyrrolo[2,3-b]pyridin-4-yl]imidazo[1,2-b]pyridazine in 10 ml of a mixture of methanol and a few ml of tetrahydrofuran is 0.32 ml (1.9 mmol) of a 6N aqueous solution of sodium hydroxide. The mixture gradually become homogeneous and the reaction is stirred for 30 minutes. The reaction medium is diluted with 100 ml of water and the product is extracted with dichloromethane. The organic phase is separated, dried over sodium sulphate and the solvent is removed by evaporation under reduced pressure. The orange solid obtained is then chromatographed over a silica gel column (35 g) by eluting with a mixture of dichloromethane, methanol and aqueous ammonia (95/5/0.5) in order to give 0.293 g of 6-chloro-2-(4-fluorophenyl)-8-methyl-3-(1H-pyrrolo[2,3-b]pyridin-4-yl)imidazo[1,2-b]pyridazine in the form of a yellow powder after trituration in isopropyl ether, chilling, filtration and drying.

MP: 226-228° C.

$^1$H NMR (CDCl$_3$) δ: 9.5 (sl, 1H); 8.40 (d, 1H); 7.55 (d, 2H); 7.30 (d, 1H); 7.2 (m, 1H); 6.9 (m, 3H); 5.90 (m, 1H); 2.70 (s, 3H) ppm.

Step 1.6 (Cis)-2-(4-Fluorophenyl)-8-methyl-6-[(cis)-5-methylhexahydropyrrolo[3,4-c]pyrrol-2(1H)-yl]-3-(1H-pyrrolo[2,3-b]pyridin-4-yl)imidazo[1,2-b]pyridazine

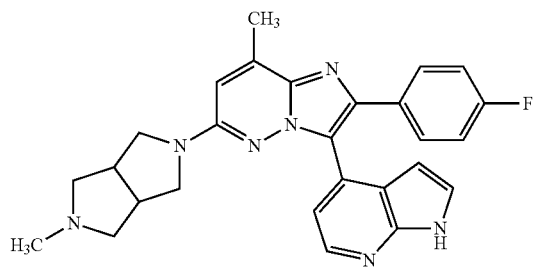 [SMILES: Cc1cc(N2CC3CN(C)CC3C2)nn2c(-c3ccnc4[nH]ccc34)c(-c3ccc(F)cc3)nc12]

In a sealed tube the mixture of 0.29 g (0.77 mmol) of 6-chloro-2-(4-fluorophenyl)-8-methyl-3-(1H-pyrrolo[2,3-b]pyridin-4-yl)imidazo[1,2-b]pyridazine, 0.12 g (0.92 mmol) of (cis)-octahydro-6H-2-methylpyrrolo[3,4-c]pyrrole (CAS 172739-03-6) and 0.11 ml (0.77 mmol) of triethylamine in 4 ml of pentanol is heated at 150° C. for 26 hours. After cooling, the reaction mixture is poured into 60 ml of a 1N aqueous solution of hydrochloric acid and the solution is washed with ethyl acetate. The aqueous phase is then basified by addition of aqueous ammonia and the product is extracted with dichloromethane. The organic phase is separated, dried over sodium sulphate and the solvent is removed by evaporation under reduced pressure. The chestnut brown oil obtained is then chromatographed over a silica gel column (35 g) by eluting with a mixture of dichloromethane, methanol and aqueous ammonia (90/10/1) in order to give 0.101 g of 2-(4-fluorophenyl)-8-methyl-6-[(cis)-5-methylhexahydropyrrolo[3,4-c]pyrrol-2(1H)-yl]-3-(1H-pyrrolo[2,3-b]pyridin-4-yl)imidazo[1,2-b]pyridazine in the form of a beige powder after trituration in diethyl ether, chilling, filtration and drying.

MP: 255° C. (decomposition)

$^1$H NMR (DMSO-d$_6$) δ: 11.7 (s, 1H); 8.35 (d, 1H); 7.50 (m, 2H); 7.40 (d, 1H); 7.30 (d, 1H); 7.1 (pt, 2H); 6.90 (m, 1H); 5.90 (d, 1H); 3.50 (m, 2H); 3.20 (dd, 2H); 2.85 (m, 2H); 2.60 (s, 3H); 2.45 (m, 2H); 2.40 (m, 2H); 2.20 (s, 3H) ppm.

EXAMPLE 2

Compound No. 1

2-Methyl-6-[(R)-3-methylpiperazin-1-yl]-3-(1H-pyrrolo[2,3-b]pyridin-4-yl)imidazo[1,2-b]pyridazine

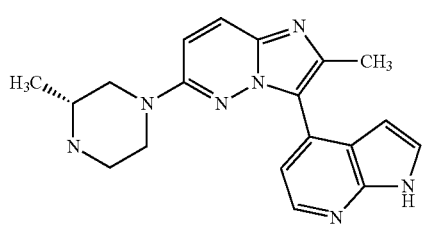 [SMILES: Cc1nc2ccc(N3CCN[C@H](C)C3)nn2c1-c1ccnc2[nH]ccc12]

Step 2.1.
6-Chloro-3-iodo-2-methylimidazo[1,2-b]pyridazine

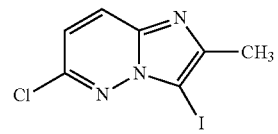

Added to a solution of 7.00 g (41.8 mmol) of 6-chloro-2-methylimidazo[1,2-b]pyridazine (CAS 14793-00-1) in 300 ml of chloroform, cooled to 0° C., are 10.2 g (62.7 mmol) of iodine monochloride in solution in 20 ml of methanol. The reaction is then left at ambient temperature for 16 hours then poured over a mixture of a 5% sodium thiosulphate solution and of sodium hydrogen carbonate. The product is extracted with dichloromethane, the organic phase is dried over sodium sulphate and the solvent is evaporated under reduced pressure.

The solid residue is triturated with acetonitrile, then isolated by filtration in order to give, after drying, 8.5 g of 6-chloro-3-iodo-2-methylimidazo[1,2-b]pyridazine in the form of a yellow solid.

$^1$H NMR (CDCl$_3$) δ: 7.80 (d, 1H); 7.10 (d, 1H); 2.55 (s, 3H) ppm.

Step 2.2. 6-Chloro-2-methyl-3-{1-[(4-methylphenyl)sulphonyl]-1H-pyrrolo[2,3-b]pyridin-4-yl}imidazo[1,2-b]pyridazine

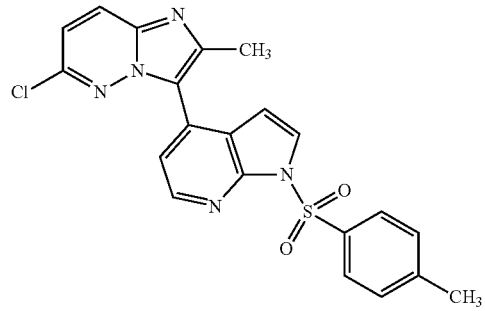 [SMILES: Cc1ccc(S(=O)(=O)n2ccc3c(-c4c(C)nc5ccc(Cl)nn45)ccnc32)cc1]

Added to a mixture, which has been previously degassed and is under argon, of 0.470 g (1.60 mmol) of 6-chloro-3-iodo-2-methylimidazo[1,2-b]pyridazine, 0.765 g (1.92 mmol) of 1-[(4-methylphenyl)sulphonyl]-4-(4,4,5,5-tetramethyl-1,3,2-dioxaborolan-2-yl)-1H-pyrrolo[2,3-b]pyridine (CAS 916176-50-6) and 1.56 g (4.80 mmol) of caesium carbonate in 10 ml of a mixture of tetrahydrofuran and water (9/1), is 0.12 g (0.14 mmol) of a complex of [1,1'-bis(diphenylphosphino)ferrocene]palladium(II) dichloride and of dichloromethane. The mixture is heated under reflux for 18 hours, then poured into 100 ml of water. The product is extracted with dichloromethane. The organic phase is separated, dried over sodium sulphate and the solvent is removed by evaporation under reduced pressure. The chestnut brown solid obtained is then chromatographed over an aminopropyl-grafted silica gel column (SiNH$_2$; 30 g) by eluting with a mixture of dichloromethane and petroleum ether (70/30) in order to give 0.42 g of 6-chloro-2-methyl-3-{1-[(4-methylphenyl)sulphonyl]-1H-pyrrolo[2,3-b]pyridin-4-yl}imidazo[1,2-b]pyridazine in the form of a white powder.

MP: 138-140° C.

$^1$H NMR (CDCl$_3$) δ: 8.50 (d, 1H); 8.10 (d, 2H); 7.85 (d, 1H); 7.75 (d, 1H); 7.25 (d, 2H); 7.05 (d, 1H); 6.30 (d, 1H); 2.45 (s, 3H); 2.35 (s, 3H) ppm.

Step 2.3. 2-Methyl-6-[(R)-3-methylpiperazin-1-yl]-3-{1-[(4-methylphenyl)sulphonyl]-1H-pyrrolo[2,3-b]pyridin-4-yl}imidazo[1,2-b]pyridazine

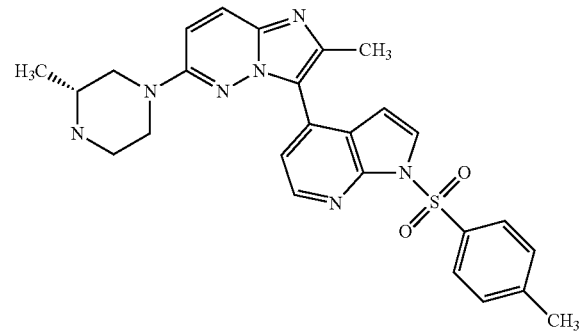

A mixture of 0.325 g (0.97 mmol) of 6-chloro-2-methyl-3-{1-[(4-methylphenyl)sulphonyl]-1H-pyrrolo[2,3-b]pyridin-4-yl}imidazo[1,2-b]pyridazine, 0.15 g (1.5 mmol) of (2R)-2-methylpiperazine and 0.10 ml (0.74 mmol) of triethylamine in 5 ml of pentanol is heated under reflux for 3 days at 150° C. The reaction medium is diluted with 100 ml of a 1N aqueous solution of hydrochloric acid and the solution is washed with ethyl acetate. The aqueous phase is then basified by addition of aqueous ammonia and the product is extracted with dichloromethane. The organic phase is separated, dried over sodium sulphate and the solvent is removed by evaporation under reduced pressure. The chestnut brown oil obtained is then chromatographed over a silica gel column (35 g) by eluting with a mixture of dichloromethane, methanol and aqueous ammonia (90/10/1) in order to give 0.293 g of 2-methyl-6-[(3R)-3-methylpiperazin-1-yl]-3-{1-[(4-methylphenyl)sulphonyl]-1H-pyrrolo[2,3-b]pyridin-4-yl}imidazo[1,2-b]pyridazine in the form of a yellow oil after drying.

$^1$H NMR (CDCl$_3$) δ: 8.60 (d, 1H); 8.20 (d, 2H); 7.80 (d, 1H); 7.75 (d, 1H); 7.40 (s, 1H); 7.35 (d, 2H); 6.90 (d, 1H); 6.55 (d, 1H); 3.8 (m, 2H); 2.9 (m, 1H); 2.7 (m, 3H); 2.40 (s, 3H); 2.35 (m, 1H); 2.25 (sl, 1H); 0.95 (d, 3H) ppm.

Step 2.4. 2-Methyl-6-[(R)-3-methylpiperazin-1-yl]-3-(1H-pyrrolo[2,3-b]pyridin-4-yl)imidazo[1,2-b]pyridazine

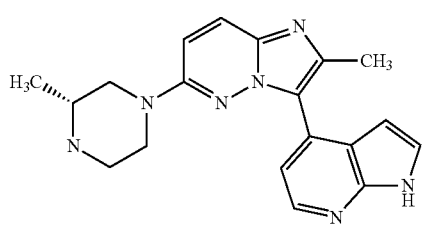 [SMILES: Cc1nc2ccc(N3CCN[C@H](C)C3)nn2c1-c1ccnc2[nH]ccc12]

Added to a solution of 0.300 g (0.60 mmol) of 2-methyl-6-[(3R)-3-methylpiperazin-1-yl]-3-{1-[(4-methylphenyl)sulphonyl]-1H-pyrrolo[2,3-b]pyridin-4-yl}imidazo[1,2-b]pyridazine in 5 ml of methanol is 0.20 ml (1.6 mmol) of a 6N aqueous solution of sodium hydroxide.

The mixture is heated at 60° C. for 1 hour then poured into 100 ml of water. The product is extracted with dichloromethane. The organic phase is separated, dried over sodium sulphate and the solvent is removed by evaporation under reduced pressure. The residue obtained is then chromatographed over a silica gel column (15 g) by eluting with a mixture of dichloromethane, methanol and aqueous ammonia (90/10/1) in order to give 0.195 g of 2-methyl-6-[(3R)-3-methylpiperazin-1-yl]-3-(1H-pyrrolo[2,3-b]pyridin-4-yl)imidazo[1,2-b]pyridazine after trituration in diisopropyl ether, chilling, filtration and drying.

MP: 202-204° C.

[alpha]$_D$=+29.0° (CH$_3$OH, c=0.683 g/100 ml)

$^1$H NMR (CDCl$_3$) δ: 8.35 (d, 1H); 7.80 (d, 1H); 7.50 (d, 1H); 7.30 (d, 1H); 7.20 (d, 1H); 6.30 (d, 1H); 3.85 (m, 2H); 2.9 (m, 1H); 2.7 (m, 3H); 2.40 (s, 3H); 2.35 (m, 1H); 2.2 (sl, 1H); 0.95 (d, 3H) ppm.

EXAMPLE 3

Compound No. 6

2-(4-Fluorophenyl)-6-[(3R)-3-methylpiperazin-1-yl]-3-(1H-pyrrolo[2,3-b]pyridin-4-yl)imidazo[1,2-b]pyridazine

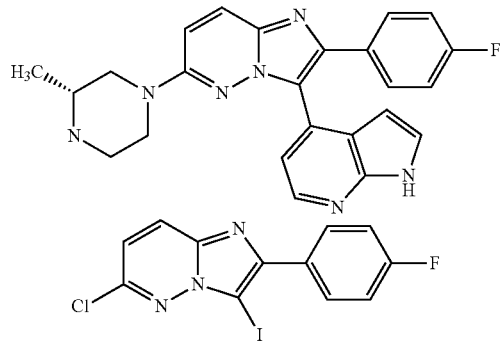

Step 3.1. 6-Chloro-2-(4-fluorophenyl)-3-iodoimidazo[1,2-b]pyridazine

A solution of 6.61 g (40.9 mmol) of iodine monochloride in 40 ml of chloroform is added in a rapid dropwise manner to a solution, cooled to 0° C., of 5.20 g (21.0 mmol) of 6-chloro-2-(4-fluorophenyl)imidazo[1,2-b]pyridazine (CAS number: 244081-70-7) in 130 ml of chloroform. After returning to ambient temperature and after stirring for 4 hours, the mixture is treated with a 5% aqueous solution of sodium thiosulphate. The product is extracted with dichloromethane, the organic phase is dried by filtration over a hydrophobic filtration cartridge and concentrated under reduced pressure. The residue is triturated in acetonitrile, the solid is isolated after filtration and rinsing with diisopropyl ether. 5.7 g of beige powder are isolated after drying under vacuum.

MP: 215° C.

$^1$H NMR (DMSO-d$_6$) δ: 8.20 (m; 3H), 7.40 (m, 3H) ppm.

Step 3.2. 6-Chloro-2-(4-fluorophenyl)-3-{1-[(4-methylphenyl)sulphonyl]-1H-pyrrolo[2,3-b]pyridin-4-yl}imidazo[1,2-b]pyridazine

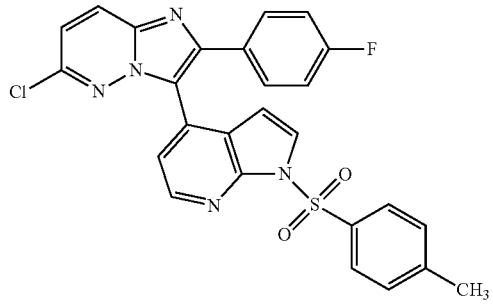 [SMILES: Cc1ccc(S(=O)(=O)n2ccc3c(-c4c(-c5ccc(F)cc5)nc5ccc(Cl)nn45)ccnc32)cc1]

Added to a mixture, which has been previously degassed and is under argon, of 0.782 g (2.09 mmol) of 6-chloro-2-(4-fluorophenyl)-3-iodoimidazo[1,2-b]pyridazine, 1.00 g (2.51 mmol) of 1-[(4-methylphenyl)sulphonyl]-4-(4,4,5,5-tetramethyl-1,3,2-dioxaborolan-2-O-1H-pyrrolo[2,3-b]pyridine (CAS 916176-50-6) and 2.05 g (6.28 mmol) of caesium carbonate in 15 ml of a mixture of tetrahydrofuran and water (9/1) is 0.15 g (0.19 mmol) of a complex of [1,1'-bis(diphenylphosphino)ferrocene]palladium(II) dichloride and of dichloromethane. The mixture is heated under reflux for 18 hours, then poured into 100 ml of water. The product is extracted with dichloromethane. The organic phase is separated, dried over sodium sulphate and the solvent is removed by evaporation under reduced pressure. The chestnut brown solid obtained is then chromatographed over an aminopropyl-grafted silica gel column (SiNH$_2$; 30 g) by eluting with a mixture of dichloromethane and petroleum ether (70/30) in order to give 0.62 g of 6-chloro-2-(4-fluorophenyl)-3-{1-[(4-methylphenyl)sulphonyl]-1H-pyrrolo[2,3-b]pyridin-4-yl}imidazo[1,2-b]pyridazine in the form of a white powder.

MP: 244-246° C.

$^1$H NMR (CDCl$_3$) δ: 8.50 (d, 1H); 8.05 (d, 2H); 7.95 (d, 1H); 7.55 (d, 1H); 7.4 (m, 3H); 7.25 (m, 2H); 7.10 (d, 1H); 6.30 (t, 2H); 5.95 (d, 1H); 2.35 (s, 3H) ppm.

Step 3.3. 2-(4-Fluorophenyl)-6-[(3R)-3-methylpiperazin-1-yl]-3-{1-[(4-methylphenyl)sulphonyl]-1H-pyrrolo[2,3-b]pyridin-4-yl}imidazo[1,2-b]pyridazine

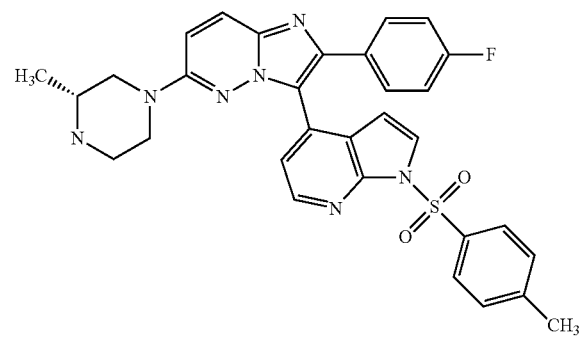

A mixture of 0.330 g (0.58 mmol) of 6-chloro-2(4-fluorophenyl)-3-{1-[(4-methylphenyl)sulphonyl]-1H-pyrrolo[2,3-b]pyridin-4-yl}imidazo[1,2-b]pyridazine, 0.116 g (1.16 mmol) of (2R)-2-methylpiperazine and 0.08 ml (0.6 mmol) of triethylamine in 5 ml of pentanol is heated under reflux for 24 hours. The reaction medium is diluted with 100 ml of an aqueous solution of hydrochloric acid and the solution is washed with ethyl acetate. The aqueous phase is then basified by addition of aqueous ammonia and the product is extracted with dichloromethane. The organic phase is separated, dried over sodium sulphate and the solvent is removed by evaporation under reduced pressure. The chestnut brown solid obtained is then purified by chromatography on a silica gel column (35 g) by eluting with a mixture of dichloromethane, methanol and aqueous ammonia (95/5/0.5) in order to give 0.232 g of 2-(4-fluorophenyl)-6-[(3R)-3-methylpiperazin-1-yl]-3-{1-[(4-methylphenyl)sulphonyl]-1H-pyrrolo[2,3-b]pyridin-4-yl}imidazo[1,2-b]pyridazine in the form of a yellow powder after drying.

MP: 253-256° C.

$^1$H NMR (CDCl$_3$) δ: 8.85 (d, 1H); 8.20 (d, 2H); 7.85 (d, 1H); 7.65 (d, 1H); 7.5 (m, 3H); 7.35 (m, 2H); 7.0 (m, 3H); 6.20 (d, 1H); 3.9 (m, 2H); 3.1 (m, 1H); 2.9 (m, 3H); 2.55 (m, 1H); 2.50 (s, 3H); 1.8 (sl); 1.10 (d, 3H) ppm.

Step 3.4. 2-(4-Fluorophenyl)-6-[(3R)-3-methylpiperazin-1-yl]-3-(1H-pyrrolo[2,3-b]pyridin-4-yl)imidazo[1,2-b]pyridazine

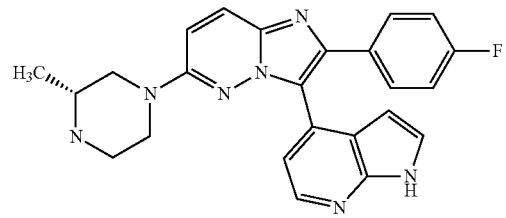 [SMILES: C[C@@H]1CN(c2ccc3nc(-c4ccc(F)cc4)c(-c4ccnc5[nH]ccc45)n3n2)CCN1]

Added to a solution of 0.230 g (0.40 mmol) of 2-(4-fluorophenyl)-6-[(3R)-3-methylpiperazin-1-yl]-3-{1-[(4-methylphenyl)sulphonyl]-1H-pyrrolo[2,3-b]pyridin-4-yl}imidazo[1,2-b]pyridazine obtained in step 3.3, in 5 ml of methanol, is 0.13 ml (0.76 mmol) of a 6N aqueous solution of sodium hydroxide. The mixture is heated at 60° C. for 30 minutes then poured into 100 ml of water. The product is extracted with dichloromethane. The organic phase is separated, dried over sodium sulphate and the solvent is removed by evaporation under reduced pressure. The residue obtained is recrystallized in acetonitrile in order to give 0.156 g of 2-(4-fluorophenyl)-6-[(3R)-3-methylpiperazin-1-yl]-3-(1H-pyrrolo[2,3-b]pyridin-4-yl)imidazo[1,2-b]pyridazine after drying.

MP: 285-287° C.

[alpha]$_D$=+4.8° (dichloromethane, c=0.998 g/100 ml)

$^1$H NMR (CDCl$_3$) δ: 9.3 (sl, 1H); 8.35 (d, 1H); 7.85 (d, 1H); 7.50 (m, 2H); 7.30 (d, 1H); 7.15 (d, 1H); 6.085 (m, 4H);

6.0 (s, 1H); 3.80 (m, 2H); 3.45 (s, 1H); 2.95 (s, 1H); 2.80 (m, 3H); 2.40 (m, 2H); 1.00 (d, 3H) ppm.

EXAMPLE 4

Compound No. 13

2-{4-[2-(4-Fluorophenyl)-8-methyl-3-(1H-pyrrolo[2,3-b]pyridin-4-yl)imidazo[1,2-b]pyridazin-6-yl]piperazin-1-yl}ethanol

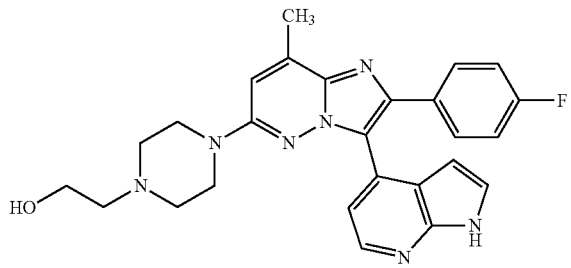 [SMILES: Cc1cc(N2CCN(CCO)CC2)nn2c(-c3ccnc4[nH]ccc34)c(-c3ccc(F)cc3)nc12]

Step 4.1. 2-{4-[2-(4-Fluorophenyl)-8-methyl-3-{1-[phenylsulphonyl]-1H-pyrrolo[2,3-b]pyridin-4-yl}imidazo[1,2-b]pyridazin-6-yl]piperazin-1-yl}ethanol

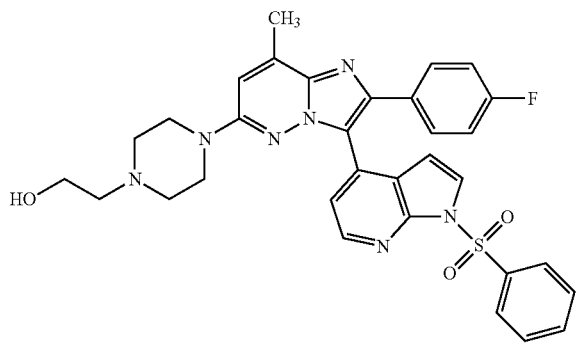 [SMILES: Cc1cc(N2CCN(CCO)CC2)nn2c(-c3ccnc4c3ccn4S(=O)(=O)c3ccccc3)c(-c3ccc(F)cc3)nc12]

A mixture of 0.530 g (1.02 mmol) of 6-chloro-2-(4-fluorophenyl)-8-methyl-3-[1-(phenylsulphonyl)-1H-pyrrolo[2,3-b]pyridin-4-yl]imidazo[1,2-b]pyridazine, prepared according to the method described in step 1.4 from Example 1, 0.266 g (2.05 mmol) of 1-(2-hydroxyethyl)piperazine (CAS 103-76-4) and 0.14 ml (1.0 mmol) of triethylamine in 5 ml of pentanol is stirred for 2 days at 150° C. The reaction medium is diluted with 20 ml of an aqueous solution of hydrochloric acid and the solution is washed with ethyl acetate. The aqueous phase is then basified by addition of aqueous ammonia and the product is extracted with dichloromethane. The organic phase is separated, dried over sodium sulphate and the solvent is removed by evaporation under reduced pressure. The brown oil obtained is then purified by chromatography on a silica gel column (40 g) by eluting with a mixture of dichloromethane, methanol and aqueous ammonia (95/5/0.5) in order to give 0.220 g of 2-{4-[2-(4-fluorophenyl)-8-methyl-3-{1-[phenylsulphonyl]-1H-pyrrolo[2,3-b]pyridin-4-yl}imidazo[1,2-b]pyridazin-6-yl]piperazin-1-yl}ethanol in the form of an amorphous powder which is used in the following step.

$^1$H NMR (CDCl$_3$) δ: 8.40 (d, 1H); 8.15 (d, 2H); 7.6-7.3 (m, 7H); 6.85 (pt, 2H); 6.65 (s, 1H); 6.05 (d, 1H); 3.6 (m, 2H); 3.3 (m, 4H); 2.6 (s, 3H); 2.5 (m, 6H) ppm.

Step 4.2. 2-{4-[2-(4-Fluorophenyl)-8-methyl-3-(1H-pyrrolo[2,3-b]pyridin-4-yl)imidazo[1,2-b]pyridazin-6-yl]piperazin-1-yl}ethanol

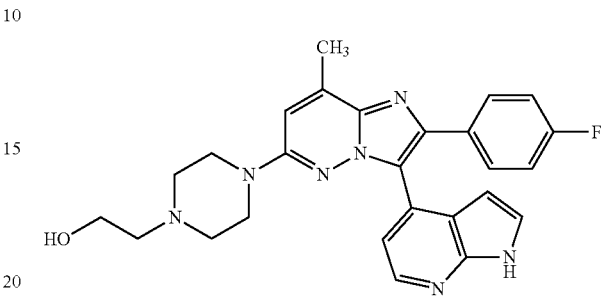

Added to a solution of 0.22 g (0.36 mmol) of 2-{4-[2-(4-fluorophenyl)-8-methyl-3-{1-[phenylsulphonyl]-1H-pyrrolo[2,3-b]pyridin-4-yl}imidazo[1,2-b]pyridazin-6-yl]piperazin-1-yl}ethanol in 5 ml of a mixture of tetrahydrofuran and methanol (1/1), is 0.12 ml (0.72 mmol) of a 6N aqueous solution of sodium hydroxide. The mixture is heated at 50° C. for 1 hour, then poured into 20 ml of water. The product is extracted with dichloromethane. The organic phase is separated, dried over sodium sulphate and the solvent is removed by evaporation under reduced pressure. The yellowish residue obtained is then purified by chromatography on a silica gel column (40 g) by eluting with a mixture of dichloromethane, methanol and aqueous ammonia (95/5/0.5) in order to give 0.110 g of 2-{4-[2-(4-fluorophenyl)-8-methyl-3-(1H-pyrrolo[2,3-b]pyridin-4-yl)imidazo[1,2-b]pyridazin-6-yl]piperazin-1-yl}ethanol after crystallization in 10 ml of acetonitrile, filtration and drying.

MP: 239-242° C.

$^1$H NMR (CDCl$_3$) δ: 8.35 (d, 1H); 7.55 (2 d, 2H); 7.40 (d, 1H); 7.30 (d, 1H); 7.20 (s, 1H); 7.10 (pt, 2H); 5.90 (d, 1H); 4.40 (t, 1H); 3.50 (m, 2H); 3.3 (m, 4H); 2.60 (s, 3H); 2.50 (m, 4H); 2.40 (t, 2H) ppm.

EXAMPLE 5

Compound No. 35

9-[2-(4-Fluorophenyl)-3-(1H-pyrrolo[2,3-b]pyridin-4-yl)imidazo[1,2-b]pyridazin-6-yl]-2,9-diazaspiro[5.5]undecane

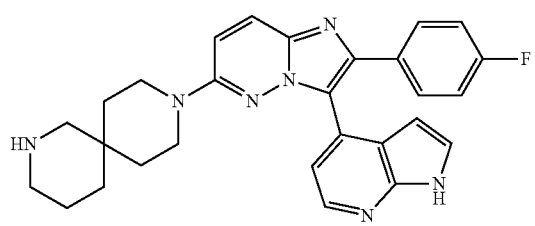 [SMILES: Fc1ccc(-c2nc3ccc(N4CCC5(CCCNC5)CC4)nn3c2-c2ccnc3[nH]ccc23)cc1]

Step 5.1. Tert-butyl 9-{2-(4-fluorophenyl)-3-[1-(4-methylphenylsulphonyl)-1H-pyrrolo[2,3-b]pyridin-4-yl]imidazo[1,2-b]pyridazin-6-yl}-2,9-diazaspiro[5.5]undecane-2-carboxylate

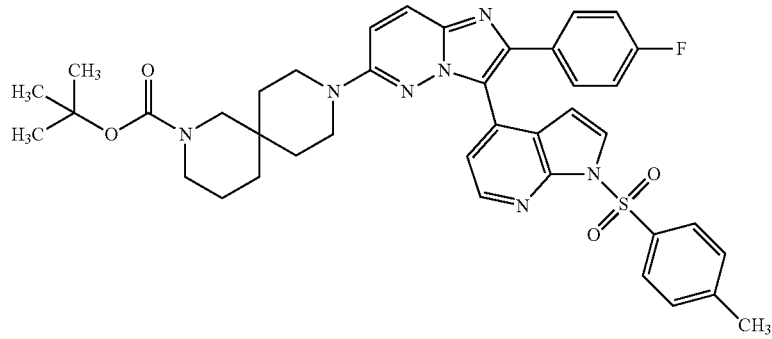 [SMILES: Cc1ccc(S(=O)(=O)n2ccc3c(-c4c(-c5ccc(F)cc5)nc5ccc(N6CCC7(CCCN(C(=O)OC(C)(C)C)C7)CC6)nn45)ccnc32)cc1]

A mixture of 0.15 g (0.29 mmol) of 6-chloro-2-(4-fluorophenyl)-3-[1-(4-methylphenylsulphonyl)-1H-pyrrolo[2,3-b]pyridin-4-yl]imidazo[1,2-b]pyridazine, prepared according to the method described in step 3.2 of Example 3, 0.337 g (1.15 mmol) of tert-butyl 2,9-diazaspiro[5.5]undecane-2-carboxylate hydrochloride (1:1) (CAS 1023301-88-3) and 0.224 g (1.7 mmol) of diisopropylethylamine in 2 ml of pentanol is heated under reflux for 40 hours at 140° C. The solvent is then evaporated under reduced pressure and the residue is purified by chromatography on a silica gel column by eluting with a gradient of dichloromethane, methanol and aqueous ammonia (of 100/0/0 to 90/10/1) in order to give 0.190 mg of tert-butyl 9-{2-(4-fluorophenyl)-3-[1-(4-methylphenylsulphonyl)-1H-pyrrolo[2,3-b]pyridin-4-yl]imidazo[1,2-b]pyridazin-6-yl}-2,9-diazaspiro[5.5]undecane-2-carboxylate after crystallization in methanol.

Step 5.2. Tert-butyl 9-[2-(4-fluorophenyl)-3-(1H-pyrrolo[2,3-b]pyridin-4-yl)imidazo[1,2-b]pyridazin-6-yl]-2,9-diazaspiro[5.5]undecane-2-carboxylate

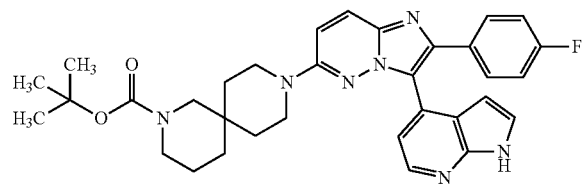 [SMILES: CC(C)(C)OC(=O)N1CCCC2(CCN(c3ccc4nc(-c5ccc(F)cc5)c(-c5ccnc6[nH]ccc56)n4n3)CC2)C1]

The tert-butyl 9-{2-(4-fluorophenyl)-3-[1-(4-methylphenylsulphonyl)-1H-pyrrolo[2,3-b]pyridin-4-yl]imidazo[1,2-b]pyridazin-6-yl}-2,9-diazaspiro[5.5]undecane-2-carboxylate obtained in step 5.1 is dissolved in 3 ml of a mixture of methanol and tetrahydrofuran (2/1) and is treated using 0.09 ml (0.54 mmol) of a 6N aqueous solution of sodium hydroxide at 60° C. for 1 and a half hours. The solvent is evaporated under reduced pressure and the residue taken up in 3 ml of water. The product is extracted 2 times with 3 ml of dichloromethane. The organic phase is dried over sodium sulphate and the solvent is removed by evaporation under reduced pressure. The residue obtained is then purified by chromatography on a silica gel column (4 g) by eluting with a gradient of dichloromethane, methanol and aqueous ammonia (of 95/5/05 to 90/10/1) in order to give 0.06 g of tert-butyl 9-[2-(4-fluorophenyl)-3-(1H-pyrrolo[2,3-b]pyridin-4-yl)imidazo[1,2-b]pyridazin-6-yl]-2,9-diazaspiro[5.5]undecane-2-carboxylate after crystallization in 10 ml of acetonitrile, filtration and drying.

MP: 192-193° C.

M+H=582

$^1$H NMR (DMSO-$d_6$) δ: 8.35 (d, 1H); 7.95 (d, 1H); 7.50 (m, 2H); 7.40 (d, 1H); 7.30 (m, 2H); 7.10 (pt, 2H); 5.85 (d, 1H); 3.55 (sl); 3.40-3.10 (m); 1.2-15 (m) ppm.

Step 5.3. 9-[2-(4-Fluorophenyl)-3-(1H-pyrrolo[2,3-b]pyridin-4-yl)imidazo[1,2-b]pyridazin-6-yl]-2,9-diazaspiro[5.5]undecane

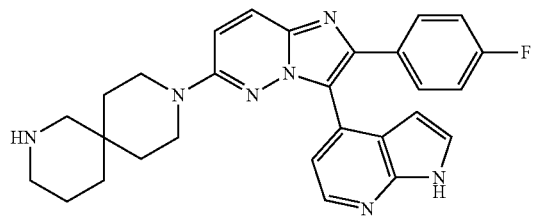 [SMILES: Fc1ccc(-c2nc3ccc(N4CCC5(CCCNC5)CC4)nn3c2-c2ccnc3[nH]ccc23)cc1]

0.20 mg (0.34 mmol) of tert-butyl 9-[2-(4-fluorophenyl)-3-(1H-pyrrolo[2,3-b]pyridin-4-yl)imidazo[1,2-b]pyridazin-6-yl]-2,9-diazaspiro[5.5]undecane-2-carboxylate are treated with 5 ml of aqueous 3N hydrochloric acid over 18 hours at ambient temperature. The reaction medium is poured into 20 ml of water and is neutralized by addition of concentrated sodium hydroxide. The product is then extracted with dichloromethane, then the organic phase is dried over sodium sulphate and the solvent is removed by evaporation under reduced pressure.

The residue obtained is then purified by chromatography on a silica gel column by eluting with a mixture of dichloromethane, methanol and aqueous ammonia (90/10/1) in order to give 0.07 g of 9-[2-(4-fluorophenyl)-3-(1H-pyrrolo[2,3-b]pyridin-4-yl)imidazo[1,2-b]pyridazin-6-yl]-2,9-diazaspiro[5,5]undecane.

MP: 279-280° C.

¹H NMR (DMSO-d₆) δ: 11.7 (s, 1H); 8.35 (d, 1H); 7.95 (d, 1H); 7.50 (m, 2H); 7.40 (d, 1H); 7.30 (m, 2H); 7.10 (pt, 2H); 5.90 (d, 1H); 3.4-3.25 (2 m, 4H); 2.6 (m, 4H); 1.6-1.35 (2 m, 8H) ppm.

EXAMPLE 6

Compound No. 36

2-(4-Fluorophenyl)-6-(4-pyrrolidin-1-ylpiperidin-1-yl)-3-(1H-pyrrolo[2,3-b]pyridin-4-yl)imidazo[1,2-b]pyridazine

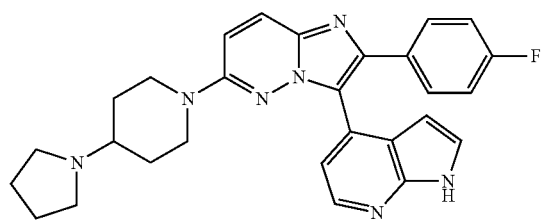 [SMILES: Fc1ccc(-c2nc3ccc(N4CCC(N5CCCC5)CC4)nn3c2-c2ccnc3[nH]ccc23)cc1]

Step 6.1. 2-(4-Fluorophenyl)-6-(4-pyrrolidin-1-ylpiperidin-1-yl)-3-[1-(4-methylphenylsulphonyl)-1H-pyrrolo[2,3-b]pyridin-4-yl]imidazo[1,2-b]pyridazine

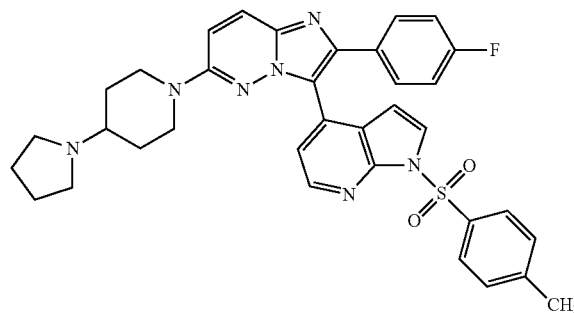

A mixture of 0.15 g (0.29 mmol) of 6-chloro-2-(4-fluorophenyl)-3-[1-(4-methylphenylsulphonyl)-1H-pyrrolo[2,3-b]pyridin-4-yl]imidazo[1,2-b]pyridazine, prepared according to the method described in step 3.2 of Example 3, and 0.179 g (1.16 mmol) of 4-pyrrolidin-1-ylpiperidine is heated under reflux for 40 hours at 140° C. The reaction medium is cooled. The crystalline solid which forms on cooling is triturated in 1 ml of diisopropyl ether and is isolated by centrifugation and removal of the supernatant in order to give 0.144 g of 2-(4-fluorophenyl)-6-(4-pyrrolidin-1-ylpiperidin-1-yl)-3-[1-(4-methylphenylsulphonyl)-1H-pyrrolo[2,3-b]pyridin-4-yl]imidazo[1,2-b]pyridazine, used without additional purification in the remainder of the synthesis.

M+H=636

Step 6.2. 2-(4-Fluorophenyl)-6-(4-pyrrolidin-1-ylpiperidin-1-yl)-3-(1H-pyrrolo[2,3-b]pyridin-4-yl)imidazo[1,2-b]pyridazine

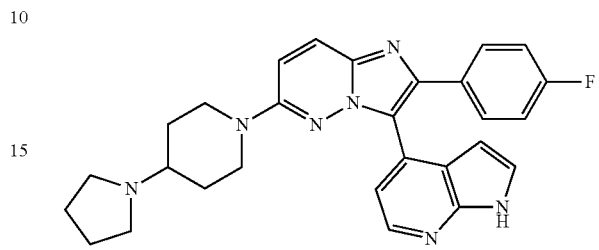

The 2-(4-fluorophenyl)-6-(4-pyrrolidin-1-ylpiperidin-1-yl)-3-[1-(4-methylphenylsulphonyl)-1H-pyrrolo[2,3-b]pyridin-4-yl]imidazo[1,2-b]pyridazine obtained in step 6.1 is dissolved in 3 ml of a mixture of methanol and tetrahydrofuran (2/1), then treated using 0.09 ml (0.54 mmol) of a 6N aqueous solution of sodium hydroxide at 60° C. for 1 and a half hours. The solvent is evaporated and the residue taken up in 3 ml of water. The product is extracted 2 times with 3 ml of dichloromethane. The organic phase is dried over sodium sulphate and the solvent is removed by evaporation under reduced pressure. The residue obtained is then purified by chromatography over a silica gel column (4 g) by eluting with a gradient of dichloromethane, methanol and aqueous ammonia (of 95/5/05 to 90/10/1) in order to give 0.064 g of 2-(4-fluorophenyl)-6-(4-pyrrolidin-1-ylpiperidin-1-yl)-3-(1H-pyrrolo[2,3-b]pyridin-4-yl)imidazo[1,2-b]pyridazine after crystallization in 10 ml of acetonitrile, filtration and drying.

MP: 261-264° C.

M+H=582

¹H NMR (DMSO-d₆) δ: 11.7 (s, 1H); 8.35 (d, 1H); 7.95 (d, 1H); 7.50 (m, 2H); 7.40 (d, 1H); 7.30 (m, 2H); 7.10 (pt, 2H); 5.85 (d, 1H); 2.9 (m, 2H); 2.45 (m, 4H); 2.15 (m, 1H); 1.85 (m, 2H); 1.7 (m, 4H), 1.4 (m, 2H) ppm.

EXAMPLE 7

Compound No. 16

(R)-1-{4-[2-(4-Fluorophenyl)-8-methyl-3-(1H-pyrrolo[2,3-b]pyridin-4-yl)imidazo[1,2-b]pyridazin-6-yl]piperazin-1-yl}propan-2-ol

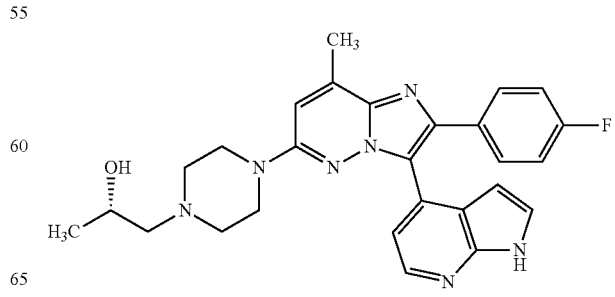

Step 7.1. (R)-1-(4-Benzylpiperazin-1-yl)-2-hydroxypropan-1-one

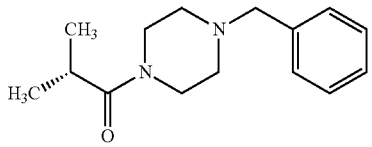

A mixture of 10.3 g (87.2 mmol) of ethyl (R)-lactate (CAS 7699-00-5) and 15.3 g of benzylpiperazine (CAS 2759-28-6) is heated at 150° C. in a microwave oven for 2 hours. The reaction medium is cooled and is chromatographed over a silica gel cartridge by eluting with a mixture of ethyl acetate and methanol (99/1 then 98/2) in order to lead to 10 g of (R)-1-(4-benzylpiperazin-1-yl)-2-hydroxypropan-1-one in the form of a brown oil.

[alpha]$_D$=+2.4° (methanol, c=1 g/100 ml)
$^1$H NMR (DMSO-d$_6$) δ: 7.35 (m, 5H); 4.45 (m, 1H); 3.85 (m, 1H); 3.7 (m, 2H); 3.55 (s, 2H); 3.45 (m, 2H); 2.5 (m, 4H); 1.35 (d, 3H) ppm.

Step 7.2. (R)-1-(4-Benzylpiperazin-1-yl)propan-2-ol

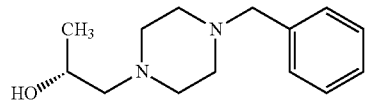 [SMILES: C[C@@H](O)CN1CCN(Cc2ccccc2)CC1]

Added dropwise, over 20 minutes, to a suspension of 3.9 g (103 mmol) of lithium aluminium hydride in 200 ml of tetrahydrofuran, at 20° C. and with stirring, are 12.8 g (51.7 mmol) of (R)-1-(4-benzylpiperazin-1-yl)-2-hydroxypropan-1-one in solution in 100 ml of tetrahydrofuran. An increase in the temperature of the reaction medium was observed up to 35° C. and the temperature of the reaction was left to drop back down to ambient temperature. After 30 minutes, the excess of hydride is hydrolysed by addition of hydrated sodium sulphate, the mixture is then filtered and the solid residue is washed with tetrahydrofuran. The filtrate is concentrated under reduced pressure in order to give 11 g of a yellow oil which is chromatographed over a silica gel cartridge by eluting with a mixture of ethyl acetate, methanol and aqueous ammonia (95/5/0.5) in order to result in 6.4 g of (R)-1-(4-benzylpiperazin-1-yl)propan-2-ol in the form of a yellow oil.

[alpha]$_D$=−20.5° (methanol, c=0.1 g/100 ml)
$^1$H NMR (CDCl$_3$) δ: 7.25 (m, 5H); 4.20 (d, 1H); 3.70 (m, 1H); 3.45 (s, 2H); 2.4 and 2.2 (m, 10H); 1.0 (d, 3H) ppm.

Step 7.3. (R)-1-(piperazin-1-yl)propan-2-ol dihydrochloride

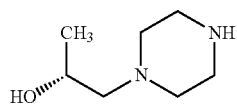

A solution of 6.2 g (26.5 mmol) of (R)-1-(4-benzylpiperazin-1-yl)propan-2-ol in 60 ml of methanol is hydrogenated under a hydrogen pressure of 60 psi at ambient temperature for 2 hours in the presence of 2.95 g of palladium hydroxide-on-carbon (CAS 12135-22-7). The mixture is then filtered through a Büchner funnel and the filtrate is concentrated under a reduced pressure to give 3.8 g of yellow oil. The oil is diluted in around 60 ml of isopropanol and the solution is acidified by addition of 5-6N hydrochloric acid in solution in isopropanol. The precipitate is stirred for 15 minutes and is isolated by filtration in order to give, after drying, 4.97 g of (R)-1-(piperazin-1-yl)propan-2-ol dihydrochloride in the form of a white powder.

MP: 222-224° C.
[alpha]$_D$=−29.2° (methanol, c=1 g/100 ml)
$^1$H NMR (CDCl$_3$) δ: 3.8 (m, 1H); 2.9 (m, 3H); 2.65 (m, 4H); 2.35 and 2.2 (m and m, 3H); 1.15 (d, 3H) ppm.

Step 7.4. (R)-1-{4-[2-(4-Fluorophenyl)-8-methyl-3-(1H-pyrrolo[2,3-b]pyridin-4-yl)-imidazo[1,2-b]pyridazin-6-yl]piperazin-1-yl}propan-2-ol

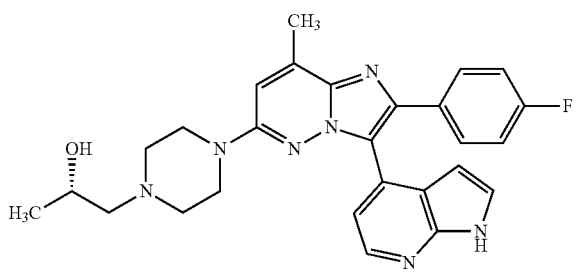 [SMILES: Cc1cc(N2CCN(C[C@H](C)O)CC2)nn2c(-c3ccnc4[nH]ccc34)c(-c3ccc(F)cc3)nc12]

A solution of 0.450 g (1.19 mmol) of 6-chloro-2-(4-fluorophenyl)-8-methyl-3-(1H-pyrrolo[2,3-b]pyridin-4-yl)imidazo[1,2-b]pyridazine, prepared according to the method described in step 1.5 of Example 1, 0.517 g (2.38 mmol) of (R)-1-(piperazin-1-yl)propan-2-ol dihydrochloride and 0.98 ml of diisopropylethylamine in 5 ml of dimethylsulphoxide is heated at 85° C. for 7 days. After cooling, the reaction mixture is poured into water and the product is extracted with ethyl acetate. The organic phase is then dried over sodium sulphate, then concentrated under reduced pressure. The brown residue obtained is then purified by chromatography over silica gel by eluting with a mixture of dichloromethane, methanol and aqueous ammonia (95/5/0.5) in order to result in 0.04 g of (R)-1-{4-[2-(4-fluorophenyl)-8-methyl-3-(1H-pyrrolo[2,3-b]pyridin-4-yl)imidazo[1,2-b]pyridazin-6-yl]piperazin-1-yl}propan-2-ol after recrystallization in 40 ml of acetonitrile, filtration and drying.

MP: >350° C.
[alpha]$_D$=−12.6° (methanol, c=0.09 g/100 ml)
$^1$H NMR (DMSO-d$_6$) δ: 11.7 (broad s, 1H); 8.35 (d, 1H); 7.50 (m, 2H); 7.40 (m, 1H); 7.30 (dd, 1H); 7.20 (s, 1H); 7.10

(m, 2H); 5.85 (m, 1H); 4.30 (m, 1H); 3.80 (m, 1H); 3.35 (m, 4H+H$_2$O); 2.60 (s, 3H); 2.40 (m, 4H+DMSOd$_5$); 2.25 (m, 2H); 1.05 (d, 3H).

EXAMPLE 8

Compound No. 17

(S)-1-{4-[2-(4-Fluorophenyl)-8-methyl-3-(1H-pyrrolo[2,3-b]pyridin-4-yl)imidazo[1,2-b]pyridazin-6-yl]piperazin-1-yl}propan-2-ol

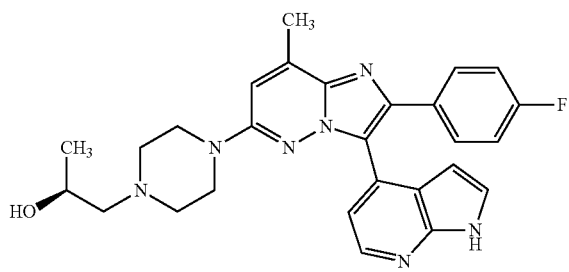 [SMILES: Cc1cc(N2CCN(C[C@H](C)O)CC2)nn2c(-c3ccnc4[nH]ccc34)c(-c3ccc(F)cc3)nc12]

Step 8.1. (S)-1-(4-Benzylpiperazin-1-yl)-2-hydroxypropan-1-one

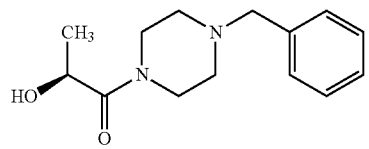 [SMILES: C[C@H](O)C(=O)N1CCN(Cc2ccccc2)CC1]

A mixture of 6.00 g (50.8 mmol) of ethyl (S)-lactate (CAS 687-47-8) and 9.85 g (50.8 mmol) of benzylpiperazine (CAS 2759-28-6) is heated at 140° C. in a microwave oven (300 W) for 1 hour. The reaction medium is cooled, then it is chromatographed over a silica gel cartridge by eluting with a mixture of dichloromethane, methanol and aqueous ammonia (95/5/0.5) in order to give 7 g of yellow oil. This oil is diluted in acetone and the (S)-1-(4-benzylpiperazin-1-yl)-2-hydroxypropan-1-one hydrochloride is formed by addition of a solution of hydrochloric acid in isopropanol. The white precipitate formed is isolated by filtration, then it is taken up in water and treated using aqueous ammonia. The product is then extracted using dichloromethane, the solution is dried over sodium sulphate and the solvent evaporated under reduced pressure in order to result in 3.7 g of (S)-1-(4-benzyl-piperazin-1-yl)-2-hydroxypropan-1-one in the form of a colourless oil.

[alpha]$_D$=−2.2° (methanol, c=1.56 g/100 ml)

$^1$H NMR (CDCl$_3$) δ: 7.25 (m, 5H); 4.35 (m, 1H); 3.75 (m, 1H); 3.6 (m, 2H); 3.45 (s, 2H); 3.35 (m, 2H); 2.4 (m, 4H); 1.25 (d, 3H) ppm.

Step 8.2. (S)-1-(4-Benzylpiperazin-1-yl)propan-2-ol

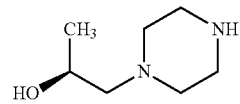

Added dropwise to a suspension of 1.13 g (29.8 mmol) of lithiumaluminium hydride in 20 ml of tetrahydrofuran, at 20° C. and with stirring, are 3.70 g (14.9 mmol) of (S)-1-(4-benzyl-piperazin-1-yl)-2-hydroxypropan-1-one in solution in 100 ml of tetrahydrofuran. The temperature of the reaction is left to drop back down to ambient temperature. After 2 hours, the excess hydride is hydrolysed by addition of hydrated sodium sulphate, then the mixture is then filtered and the filtrate is concentrated under reduced pressure. The oil obtained is chromatographed over a silica gel cartridge by eluting with a mixture of methanol and aqueous ammonia in dichloromethane (100/0/0 to 95/5/0.5) in order to result in 1.2 g of (S)-1-(4-benzy-piperazin-1-yl)propan-2-ol in the form of a yellow oil.

[alpha]$_D$=+23.2° (methanol, c=1 g/100 ml)

$^1$H NMR (CDCl$_3$) δ: 7.3 (m, 5H); 3.85 (m, 1H); 3.65 (s, 2H); 2.8-2.2 (m, 10H) 1.15 (d, 3H) ppm.

Step 8.3. (S)-1-(piperazin-1-yl)propan-2-ol

A solution of 1.2 g (5.1 mmol) of (S)-1-(4-benzylpiperazin-1-yl)propan-2-ol in 50 ml of methanol is hydrogenated under a hydrogen pressure of 50 psi at ambient temperature for 2 hours in the presence of 0.6 g of palladium hydroxide. The mixture is then filtered through a Büchner funnel and the filtrate is concentrated under reduced pressure to give 0.5 g of yellow oil.

[alpha]$_D$=+30.5° (methanol, c=1 g/100 ml)

¹H NMR (CDCl₃) δ: 3.8 (m, 1H); 2.8 (m, 4H); 2.65-2.05 (m, 8H); 1.05 (d, 3H) ppm.

Step 8.4. (S)-1-{4-[2-(4-Fluorophenyl)-8-methyl-3-(1H-pyrrolo[2,3-b]pyridin-4-yl)-imidazo[1,2-b]pyridazin-6-yl]piperazin-1-yl}propan-2-ol

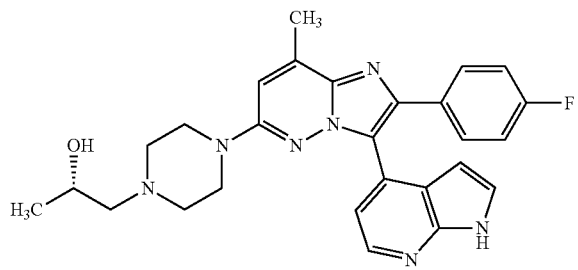 [SMILES: Cc1cc(N2CCN(C[C@H](C)O)CC2)nn2c(-c3ccnc4[nH]ccc34)c(-c3ccc(F)cc3)nc12]

A solution of 0.300 g (0.79 mmol) of 6-chloro-2-(4-fluorophenyl)-8-methyl-3-(1H-pyrrolo[2,3-b]pyridin-4-yl)imidazo[1,2-b]pyridazine, prepared according to the method described in step 1.5 of Example 1, 0.345 g (1.59 mmol) of (S)-1-(piperazin-1-yl)propan-2-ol and 0.45 ml (3.18 mmol) of diisopropylethylamine in 5 ml of pentanol is heated at 150° C. for 8 days. After cooling, the reaction mixture is poured into a 1N aqueous solution of hydrochloric acid and the aqueous phase is washed with ethyl acetate. The aqueous phase is then basified using an aqueous solution of ammonia and the product is extracted with dichloromethane. The organic phase is then dried over sodium sulphate, then concentrated under reduced pressure. The brown residue obtained is then purified by chromatography over a silica gel cartridge by eluting with a mixture of dichloromethane, methanol and aqueous ammonia (95/5/0.5) in order to result in 0.05 g of (S)-1-{4-[2-(4-fluorophenyl)-8-methyl-3-(1H-pyrrolo[2,3-b]pyridin-4-yl)imidazo[1,2-b]pyridazin-6-yl]piperazin-1-yl}propan-2-ol after recrystallization in acetonitrile, filtration and drying.

MP: >350° C.
[Alpha]$_D$=+13.9° (methanol, c=0.2 g/100 ml)
¹H NMR (DMSO-d₆) δ: 11.7 (broad s, 1H); 8.35 (d, 1H); 7.50 (m, 2H); 7.40 (m, 1H); 7.30 (dd, 1H); 7.20 (s, 1H); 7.10 (m, 2H); 5.85 (m, 1H); 4.30 (m, 1H); 3.80 (m, 1H); 3.35 (m, 4H); 2.60 (s, 3H); 2.40 (m, 4H); 2.25 (m, 2H); 1.05 (d, 3H).

Table 1 which follows illustrates the chemical structures and the physical properties of a number of compounds according to the invention.

In this table:
- in the column "Salt", "–" represents a compound in free base form, whereas "HCl" represents a compound in the hydrochloride form and the ratio between parentheses is the acid:base ratio;
- the column "MP° C." reports the melting points of the products in degrees Celsius. "ND" means that the melting point is not determined;
- the column [α]$_D$ reports the result of the analysis of the optical rotation of the compounds from the table at a wavelength of 589 nm; the solvent indicated between parentheses corresponds to the solvent used to carry out the measurement of the optical rotation in degrees and the letter "c" indicates the concentration of the solvent in g/100 ml. "N.A." signifies that the optical rotation measurement is not applicable,
- the column "m/z" reports the molecular ion (M+H⁺) or (M⁺) observed by analysis of the products by mass spectrometry, either by LC-MS (Liquid Chromatography coupled to Mass Spectroscopy) carried out on an Agilent LC-MSD Trap instrument in positive ESI mode, or by direct introduction by MS (Mass Spectroscopy) into an Autospec M (EBE) instrument using the DCl—NH₃ technique or by using the electron impact technique on a Waters GCT instrument. The values that have an asterisk "*" correspond to the detection of the ion (M⁺), "CH₃—" stands for methyl;
"CH₃OH" stands for methanol;
"CH₂Cl₂" stands for dichloromethane; and
"DMSO" stands for dimethylsulphoxide.

TABLE 1

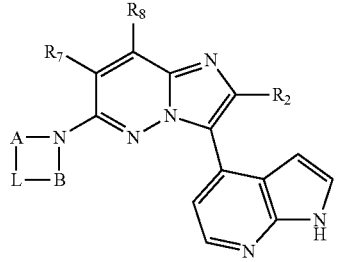

| No | NALB | R₇ | R₈ | R₂ | Salt | m/z | [α]$_D$(°) (c in g/100 ml; solvent) | MP °C. |
|---|---|---|---|---|---|---|---|---|
| 1 | (R)-3-Methylpiperazin-1-yl | H | H | CH₃— | — | 348 | +29 (c = 0.683; CH₃OH) | 202-204 |
| 2 | 3,3-Dimethylpiperazin-1-yl | H | H | CH₃— | HCl (3:1) | 362 | N.A. | 220 decomposition |
| 3 | (cis)-3,5-Dimethylpiperazin-1-yl | H | H | CH₃— | HCl (3:1) | 362 | N.A. | 235 decomposition |
| 4 | 4-Isopropylpiperazin-1-yl | H | H | CH₃— | HCl (3:1) | 376 | N.A. | 195 |
| 5 | (cis)-5-Methylhexahydropyrrolo[3,4-c]pyrrol-2(1H)-yl | H | H | CH₃— | HCl (3:1) | *373 | N.A. | 205 decomposition |

TABLE 1-continued

| No | NALB | R₇ | R₈ | R₂ | Salt | m/z | [α]$_D$(°) (c in g/100 ml; solvent) | MP °C. |
|---|---|---|---|---|---|---|---|---|
| 6 | (R)-3-Methylpiperazin-1-yl | H | H | 4-F-Phenyl | — | 428 | +4.8 (c = 0.998; CH₂Cl₂) | 285-287 |
| 7 | 3-Hydroxymethylpiperazin-1-yl | H | H | 4-F-Phenyl | — | 444 | N.A. | 234-238 |
| 8 | 3,3-Dimethylpiperazin-1-yl | H | H | 4-F-Phenyl | — | 442 | N.A. | 284-287 |
| 9 | 3,3-Dimethylpiperazin-1-yl | H | CH₃ | 3-F-Phenyl | — | 456 | N.A. | 270-273 |
| 10 | 3,3-Dimethylpiperazin-1-yl | H | CH₃ | 4-F-Phenyl | — | 456 | N.A. | >300 |
| 11 | (cis)-3,5-Dimethylpiperazin-1-yl | H | H | 4-F-Pheyln | — | 442 | N.A. | 288-290 |
| 12 | 4-(2-Hydroxyethyl)piperazin-1-yl | H | CH₃ | 3-F-Phenyl | — | 472 | N.A. | 201-203 |
| 13 | 4-(2-Hydroxyethyl)piperazin-1-yl | H | CH₃ | 4-F-Phenyl | — | 472 | N.A. | 239-242 (butanol) 187-198 (acetonitrile) |
| 14 | 4-Isopropylpiperazin-1-yl | H | H | 4-F-Phenyl | — | 456 | N.A. | 271-273 |
| 15 | 4-lsopropylpiperazin-1-yl | H | CH₃ | 4-F-Phenyl | — | 470 | N.A. | 285-291 |
| 16 | (R)-4-(2-Hydroxypropyl)-piperazin-1-yl | H | CH₃ | 4-F-Phenyl | — | 486 | −12.6 (c = 0.09; CH₃OH) | >350° C. |
| 17 | (S)-4-(2-Hydroxypropyl)-piperazin-1-yl | H | CH₃ | 4-F-Phenyl | — | 486 | +13.9(c = 0.2; CH₃OH) | >350° C. |
| 18 | 6,9-Diazaspiro[4.5]dec-9-yl | H | CH₃ | 4-F-Phenyl | — | 482 | N.A. | 293-299 |
| 19 | 4-(1-Hydroxy-2-methylpropan-2-yl)piperazin-1-yl | H | H | 4-F-Phenyl | — | 486 | N.A. | >250° C. |
| 20 | 4-(2-Hydroxy-2-methylpropyl)-piperazin-1-yl | H | H | 4-F-Phenyl | — | 486 | N.A. | 273-276 |
| 21 | 4-(2-Hydroxy-2-methylpropyl)-piperazin-1-yl | H | CH₃ | 3-F-Phenyl | — | 500 | N.A. | >270° C. |
| 22 | 4-(2-Hydroxy-2-methylpropyl)-piperazin-1-yl | H | CH₃ | 4-F-Phenyl | — | 500 | N.A. | 265-268 |
| 23 | 4-(3-Hydroxy-3-methylbutyl)-piperazin-1-yl | H | H | 4-F-Phenyl | — | 500 | N.A. | 73-75 |
| 24 | (R)-3-Phenylpiperazin-1-yl | H | H | 4-F-Phenyl | HCl (3:1) | 490 | −27 (c = 0.714; CH₃OH) | 215° C. decomposition |
| 25 | (S)-3-Phenylpiperazin-1-yl | H | H | 4-F-Phenyl | HCl (3:1) | 490 | +22 (c = 0.622; CH₃OH) | 215° C. decomposition |
| 26 | 3-Phenylpiperazin-1-yl | H | CH₃ | 4-F-Phenyl | — | 504 | N.A. | 253-257 |
| 27 | 4-Benzylpiperazin-1-yl | H | H | 4-F-Phenyl | — | 504 | N.A. | 274-278 |
| 28 | (cis)-5-Methylhexahydro-pyrrolo[3,4-c]pyrrol-2(1H)-yl | H | H | 4-F-Phenyl | — | 454 | N.A. | 238-239 |
| 29 | (cis)-5-Methylhexahydro-pyrrolo[3,4-c]pyrrol-2(1H)-yl | H | CH₃ | 4-F-Phenyl | — | 468 | N.A. | 255 decomposition |
| 30 | (cis)-5-(2-Hydroxyethyl)-hexahydropyrrolo[3,4-c]pyrrol-2(1H)-yl | H | H | 4-F-Phenyl | — | 484 | N.A. | 175-180 |
| 31 | (cis)-5-(2-Hydroxyethyl)-hexahydropyrrolo[3,4-c]pyrrol-2(1H)-yl | H | CH₃ | 4-F-Phenyl | — | 498 | N.A. | 271-275 |
| 32 | (4aR,7aR)-1-methyloctahydro-6H-pyrrolo[3,4-b]pyridine-6-yl | H | CH₃ | 4-F-Phenyl | — | 482 | +24.4 (c = 0.492; CH₃OH) | >260° C. |
| 33 | (4aS,7aS)-1-methyloctahydro-6H-pyrrolo[3,4-b]pyridin-6-yl | H | CH₃ | 4-F-Phenyl | — | 482 | −21.8 (c = 0.478; CH₃OH) | >260° C. |
| 34 | (1S,4S)-5-Methyl-2,5-diaza-bicyclo[2.2.1]hept-2-yl | H | H | 4-F-Phenyl | — | 440 | −66.0 (c = 0.961; DMSO) | 148-168 |

TABLE 1-continued

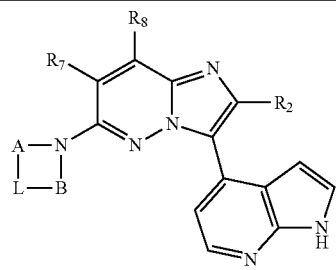

| No | NALB | R7 | R8 | R2 | Salt | m/z | [α]D(°) (c in g/ 100 ml; solvent) | MP °C. |
|---|---|---|---|---|---|---|---|---|
| 35 | 2,9-Diazaspiro[5.5]undec-9-yl | H | H | 4-F-Phenyl | — | 482 | N.A. | 279-280 |
| 36 | 4-(Pyrrolidin-1-yl)piperidin-1-yl | H | H | 4-F-Phenyl | — | 482 | N.A. | 261-264 |

BIOLOGICAL EXAMPLES

The capacity of the compounds of the invention to inhibit the phosphorylation of casein by casein kinase 1 epsilon and delta may be evaluated according to the procedure described in US 2005/0131012.

Filter-Plate Assay of ATP-$^{33}$P for the Screening of CK1 Epsilon Inhibitors:

The effect of the compounds on inhibition of the phosphorylation of casein by the enzyme casein kinase 1 epsilon (CK1 epsilon) is measured, using a casein assay with filtration of ATP-$^{33}$P in vitro.

Casein kinase 1 epsilon (0.58 mg/ml) is obtained via fermentation and purification processes performed according to methods that are well known to those skilled in the art, or may also be obtained from Invitrogen Corporation™ (human CK1 epsilon).

The compounds are tested at five different concentrations so as to generate IC$_{50}$ values, i.e. the concentration at which a compound is capable of inhibiting the enzymatic activity by 50%, or alternatively the percentage of inhibition at a concentration of 10 micromolar.

"U"-bottomed Falcon plates are prepared by placing 5 μL of solutions of the compounds according to the invention at concentrations of 10, 1, 0.1, 0.01 or 0.001 μM in various wells. The solutions of the compounds according to the invention at these various concentrations are prepared by diluting in a test buffer (50 mM Tris, pH 7.5, 10 M MgCl$_2$, 2 mM DTT and 1 mM EGTA) a stock solution in DMSO at a concentration of 10 mM. Next, 5 μL of dephosphorylated casein are added to a final concentration of 0.2 μg/μL, 20 μl of CK1 epsilon to a final concentration of 3 ng/μl, and 20 μl of ATP-$^{33}$P to a final concentration of 0.02 μCi/μl mixed with cold ATP (10 μM final—approximately 2×10$^6$ CPM per well). The final total test volume per well is equal to 50 μl.

The "U"-bottomed Falcon® test plate mentioned above is vortexed, and then incubated at ambient temperature for 2 hours. After 2 hours, the reaction is stopped by adding an ice-cold solution of 65 μl of ATP (2 mM) prepared in test buffer.

100 μl of the reaction mixture are then transferred from the "U"-bottomed Falcon® plate into Millipore® MAPH filter plates, preimpregnated with 25 μl of ice-cold 100% TCA.

The Millipore MAPH filter plates are agitated gently and are left to stand at ambient temperature for at least 30 minutes to precipitate the proteins.

After 30 minutes, the filter plates are sequentially washed and filtered with 2×150 μl of 20% TCA, 2×150 μl of 10% TCA and 2×150 μl of 5% TCA (6 washes in total per plate/900 μl per well).

The plates are left to dry overnight at ambient temperature. Next, 40 μl of Microscint-20 Packard® scintillation liquid are added per well and the plates are closed in a leaktight manner. The radiation emitted by each well is then measured for 2 minutes in a Packard® Topcount NXT scintillation counter, in which the values of CPM/well are measured.

The percentage inhibition of the capacity of the enzyme to phosphorylate the substrate (casein) is determined for each concentration of compound tested. These inhibition data expressed as percentages are used to calculate the IC$_{50}$ value for each compound compared with the controls.

The kinetic studies determined the K$_M$ value for ATP as being 21 μM in this test system.

Table 2 below gives the IC$_{50}$ values for the inhibition of phosphorylation of casein kinase 1 epsilon for a number of compounds according to the invention.

TABLE 2

| Compound No. | CK1 epsilon IC$_{50}$ (nM) |
|---|---|
| 3 | 303 |
| 6 | 1-2 |
| 35 | 6 |
| 36 | 5-8 |

Under these conditions, the most active compounds of the invention show IC$_{50}$ values (concentration which inhibits 50% of the enzymatic activity of casein kinase 1 epsilon) of between 1 nM and 2 μM.

The capacity of the compounds of the invention to inhibit the phosphorylation of casein by casein kinase 1 epsilon and delta may be evaluated using a FRET ("Fluorescence Resonance Energy Transfer) fluorescence test with the aid of the "Z'Lyte™ kinase assay Kit" (reference PV3670; Invitrogen Corporation™) according to the manufacturer's instructions.

The casein kinases 1 used are obtained from Invitrogen Corporation (human CK1 epsilon PV3500 and human CK1 delta PV3665).

A peptide substrate, labelled at both ends with a fluorophor donor group (coumarin) and a fluorophor acceptor group (fluorescein) constituting a FRET system is phosphorylated in the presence of ATP by casein kinase 1 epsilon or delta in the presence of increasing concentrations of compounds of the invention.

The mixture is treated with a site-specific protease that specifically cleaves the peptide substrate to form two fluorescent fragments having a large fluorescence emission ratio.

The fluorescence observed is thus related to the capacity of the products of the invention to inhibit the phosphorylation of the peptide substrate by casein kinase 1 epsilon or casein kinase 1 delta.

The compounds of the invention are dissolved at different concentrations starting with a 10 mM stock solution in DMSO diluted in a buffer containing 50 mM HEPS, pH 7.5, 1 m MEGTA, 0.01% Brij-35, 10 mM $MgCl_2$ for casein kinase 1 epsilon and supplemented with Trizma Base (50 mM), pH 8.0, and $NaN_3$ (0.01% final) for casein kinase 1 delta.

The phosphorylation of the peptide substrate SER/THR 11 obtained from Invitrogen Corporation™ is performed at a final concentration of 2 µM. The ATP concentration is 4 times the $K_M$, this value being 2 µM for casein kinase 1 epsilon and 4 µM for casein kinase 1 delta.

The emitted fluorescence is measured at wavelengths of 445 and 520 nm (excitation at 400 nm).

Table 3 below gives the $IC_{50}$ values for the inhibition of phosphorylation of casein kinase 1 delta for a number of compounds according to the invention.

TABLE 3

| Compound No. | CK1 delta $IC_{50}$ (nM) |
|---|---|
| 20 | 30-42 |
| 29 | 5 |
| 36 | 19 |

Under these conditions, the compounds of the invention that are the most active have $IC_{50}$ values (concentration that inhibits 50% of the enzymatic activity of casein kinase 1 delta) of between 1 nM and 2 µM.

It is thus seen that the compounds according to the invention have an inhibitory activity on the casein kinase 1 epsilon or casein kinase 1 delta enzyme.

Experimental Protocols for Circadian Cell Assay

Mper1-luc Rat-1 (P2C4) fibroblast cultures were prepared by dividing the cultures every 3-4 days (approximately 10-20% of confluence) on 150 $cm^2$ degassed polystyrene tissue culture flasks (Falcon® #35-5001) and maintained in growth medium [EMEM (Celigro #10-010-CV); 10% foetal bovine serum (FBS; Gibco #16000-044); and 50 I.U./ml of penicillin-streptomycin (Celigro #30-001-CI)] at 37° C. and under 5% $CO_2$.

Cells obtained from Rat-1 fibroblast cultures at 30-50% of confluence as described above were co-transfected with vectors containing the selection marker for resistance to zeocin for a stable transfection and a luciferase reporter gene controlled by the mPer-1 promoter. After 24 to 48 hours, the cultures were divided on 96-well plates and maintained in growth medium supplemented with 50-100 µg/ml of zeocin (Invitrogen® #45-0430) for 10-14 days. The zeocin-resistant stable transfectants were evaluated for the expression of the reporter by adding 100 µM luciferin (Promega® #E1603®) to the growth medium and by assaying the luciferase activity on a TopCount scintillation counter (Packard Model #C384V00). The Rat-1 cell clones expressing both zeocin resistance and lucerifase activity controlled by mPer1 were serum-shock synchronized with 50% horse serum [HS (Gibco® #16050-122)] and the activity of the circadian reporter was evaluated. The P2C4 clone of Mper1-luc Rat-1 fibroblasts was selected to test the compound. Mper1-luc Rat-1 (P204) fibroblasts at 40-50% of confluence, obtained according to the protocol described above, were plated out onto 96-well opaque tissue culture plates (Perkin Elmer® #6005680). The cultures are maintained in growth medium supplemented with 100 µg/ml of zeocin (Invitrogen #45-0430) until they reach 100% of confluence (48-72 h). The cultures were then synchronized with 100 µl of synchronization medium [EMEM (Cellgro #10-010-CV); 100 I.U./ml of penicillin-streptomycin (Cellgro #30-001-C1); 50% HS (Gibco #16050-122)] for 2 hours at 37° C. and under 5% $CO_2$. After synchronization, the cultures were rinsed with 100 µl of EMEM (Cellgro #10-010-CV) for 10 minutes at ambient temperature. After rinsing, the medium was replaced with 300 µl of $CO_2$-independent medium [$CO_2$I (Gibco #18045-088); 2 mM L-glutamine (Cellgro #25-005-C1); 100 U.I./ml of penicillin-streptomycin (Cellgro #30-001-C1); 100 µM luciferin (Promega #E 1603)]. The compounds of the invention tested for the circadian effects were added to $CO_2$-independent medium in DMSO at 0.3% (final concentration). The cultures were immediately closed in a leaktight manner with TopSeal-A® film (Packard #6005185) and transferred for the luciferase activity measurement. After synchronization, the test plates were maintained at 37° C. in a tissue culture incubator (Form a Scientific Model #3914). The in vivo lucerifase activity was estimated by measuring the relative light emission on a TopCount scintillation counter (Packard Model #C4V00).

The period analysis was performed either by determining the interval between the relative light emission minima over several days or by Fourier transform. The two methods produced a virtually identical period estimation on a range of circadian periods. The power is reported in CE Delta (t+1 h), which is presented as the effective micromolar concentration that induced a 1-hour prolongation of the period. The data were analysed by adjusting a hyperbolic curve to the data expressed as change of period (y-axis) as a function of the concentration of the test compound (x-axis) in the XLfit™ software and the CE Delta (t+1 h) was interpolated from this curve.

Table 4 below gives the CE Delta (t+1 h) for a number of compounds according to the invention.

TABLE 4

| Compound No. | CE Delta (t + 1 h) (nM) |
|---|---|
| 6 | 2-3 |
| 35 | 305 |
| 36 | 1-7 |

Under these conditions, the compounds of the invention that are the most active have CE Delta (t+1h) values (effective micromolar concentration that induced a 1-hour prolongation of the period) of between 1 nM and 2 µM.

By inhibiting the enzymes CK1epsilon and/or CK1delta, the compounds that are the subjects of the invention modulate the circadian periodicity, and may be useful for treating circadian rhythm disorders.

The compounds according to the invention may in particular be used for the preparation of a medicament for preventing or treating sleep disorders: circadian rhythm disorders, such as, in particular, those caused by jetlag or shift work.

Among the sleep disorders that are especially distinguished are primary sleep disorders such as dyssomnia (for example primary insomnia), parasomnia, hypersomnia (for example excessive somnolence), narcolepsy, sleep disorders related to sleep apnoea, sleep disorders related to the circadian rhythm and otherwise unspecified dyssomnias, sleep disorders associated with medical/psychiatric disorders.

The compounds that are the subjects of the invention also cause a circadian phase shift and such a property may be useful in the context of a potential monotherapy or combined therapy that is clinically effective in the case of mood disorders.

Among the mood disorders that are especially distinguished are depressive disorders (unipolar depression), bipolar disorders, mood disorders caused by a general medical complaint and also mood disorders induced by pharmacological substances.

Among the bipolar disorders that are especially distinguished are bipolar I disorders and bipolar II disorders, including in particular seasonal affective disorders.

The compounds that are the subjects of the invention, which modulate the circadian periodicity, may be useful in the treatment of anxiety and depressive disorders caused in particular by an impairment in the secretion of CRF.

Among the depressive disorders that are especially distinguished are major depressive disorders, dysthymic disorders and otherwise unspecified depressive disorders.

The compounds that are the subjects of the invention, which modulate the circadian periodicity, may be useful for preparing a medicament for treating diseases related to dependency on abuse substances such as cocaine, morphine, nicotine, ethanol or cannabis.

By inhibiting casein kinase 1 epsilon and/or casein kinase 1 delta, the compounds according to the invention may be used for preparing medicaments, in particular for preparing a medicament for preventing or treating diseases related to hyperphosphorylation of the tau protein, in particular Alzheimer's disease.

These medicaments also find their use in therapy, in particular in the treatment or prevention of diseases caused or exacerbated by the proliferation of cells, in particular tumour cells.

As tumour cell proliferation inhibitors, these compounds are useful in the prevention and treatment of liquid tumours such as leukaemias, solid tumours that are both primary and metastatic, carcinomas and cancers, in particular: breast cancer, lung cancer, small intestine cancer, colorectal cancer; cancer of the respiratory pathways, of the oropharynx and of the hypopharynx; oesophageal cancer; liver cancer, stomach cancer, cancer of the bile ducts, cancer of the gall bladder, pancreatic cancer; cancer of the urinary tracts, including kidney, urothelium and bladder; cancers of the female genital tract, including cancer of the uterus, cervical cancer, ovarian cancer, chloriocarcinoma and trophoblastoma; cancers of the male genital tract, including prostate cancer, cancer of the seminal vesicles, testicular cancer and germinal cell tumours; cancers of the endocrine glands, including thyroid cancer, pituitary cancer and cancer of the adrenal glands; skin cancers, including haemangiomas, melanomas and sarcomas, including Kaposi's sarcoma; brain, nerve, eye or meninges tumours, including astrocytomas, gliomas, glioblastomas, retinoblastomas, neurinomas, neuroblastomas, schwannomas and meningiomas; malignant haematopoietic tumours; leukaemias (Acute Lymphocytic Leukaemia (ALL), Acute Myeloid Leukaemia (AML), Chronic Myeloid Leukaemia (CML), Chronic Lymphocytic Leukaemia (CLL)), chloromas, plasmocytomas, T or B cell leukaemias, Hodgkin or non-Hodgkin lymphomas, myelomas and various malignant haemopathies.

The compounds according to the invention may also be used for the preparation of medicaments, especially for the preparation of a medicament intended for preventing or treating inflammatory diseases, such as, in particular, inflammatory diseases of the central nervous system, for instance multiple sclerosis, encephalitis, myelitis and encephalomyelitis and other inflammatory diseases, for instance vascular pathologies, atherosclerosis, joint inflammations, arthrosis and rheumatoid arthritis.

The compounds according to the invention may thus be used for the preparation of medicaments, in particular of medicaments for inhibiting casein kinase 1 epsilon and/or casein kinase 1 delta.

Thus, according to another of its aspects, a subject of the invention is medicaments which comprise a compound of formula (I), or an addition salt thereof with a pharmaceutically acceptable acid, or alternatively a hydrate or a solvate of the compound of formula (I).

According to another of its aspects, the present invention relates to pharmaceutical compositions comprising, as active principle, a compound according to the invention. These pharmaceutical compositions contain an effective dose of at least one compound according to the invention or a pharmaceutically acceptable salt, a hydrate or a solvate of said compound, and also at least one pharmaceutically acceptable excipient.

Said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt, solvate or hydrate thereof, may be administered in unit administration form, as a mixture with standard pharmaceutical excipients, to humans and animals for the prophylaxis or treatment of the above disorders or diseases.

The appropriate unit administration forms include oral-route forms such as tablets, soft or hard gel capsules, powders, granules and oral solutions or suspensions, sublingual, buccal, intratracheal, intraocular and intranasal administration forms, inhalation forms, topical, transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in tablet form may comprise the following components:

| | |
|---|---:|
| Compound according to the invention | 50.0 mg |
| Mannitol | 223.75 mg |
| Sodium croscaramellose | 6.0 mg |
| Corn starch | 15.0 mg |
| Hydroxypropylmethylcellulose | 2.25 mg |
| Magnesium stearate | 3.0 mg |

Via the oral route, the dose of active principle administered per day may reach from 0.1 to 20 mg/kg, in one or more dosage intakes.

There may be particular cases in which higher or lower dosages are appropriate; such dosages do not depart from the context of the invention. According to the usual practice, the dosage that is appropriate to each patient is determined by the practitioner according to the mode of administration and the weight and response of said patient.

According to another of its aspects, the present invention also relates to a method for treating the pathologies indicated above, which comprises the administration to a patient of an effective dose of a compound according to the invention, or a pharmaceutically acceptable salt or hydrate or solvate thereof.

The invention claimed is:

1. A compound of general formula (I):

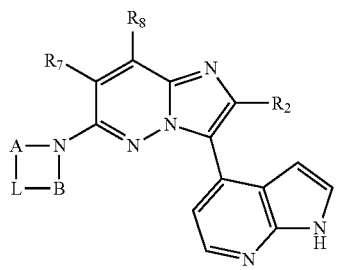

or in the form of a base or of an addition salt with an acid, in which:

$R_2$ represents an aryl group optionally substituted with one or more substituents chosen from halogen atoms and $C_{1-6}$-alkyl, $C_{1-6}$-alkyloxy, $C_{1-6}$-fluoroalkyl, $C_{1-6}$-fluoroalkyloxy and —CN groups or $R_2$ represents a $C_{1-6}$-alkyl, $C_{1-6}$-fluoroalkyl, $C_{3-7}$-cycloalkyl or $C_{3-7}$-cycloalkyl-$C_{1-6}$-alkyl group;

A represents a $C_{1-7}$-alkylene group optionally substituted with one or two $R_a$ groups;

B represents a $C_{1-7}$-alkylene group optionally substituted with an $R_b$ group;

L represents either a nitrogen atom optionally substituted with an $R_c$ or $R_d$ group, or a carbon atom substituted with an $R_{e1}$ group and an $R_d$ group or two $R_{e2}$ groups;

the carbon atoms of A and B being optionally substituted with one or more $R_f$ groups, which may be identical to or different from one another;

$R_a$, $R_b$ and $R_c$ are defined such that:
  two $R_a$ groups may together form a $C_{1-6}$-alkylene group;
  $R_a$ and $R_b$ may together form a bond or a $C_{1-6}$-alkylene group;
  $R_a$ and $R_c$ may together form a bond or a $C_{1-6}$-alkylene group;
  $R_b$ and $R_c$ may together form a bond or a $C_{1-6}$-alkylene group;

$R_d$ represents a group chosen from a hydrogen atom and $C_{1-6}$-alkyl, $C_{3-7}$-cycloalkyl, $C_{3-7}$-cycloalkyl-$C_{1-6}$-alkyl, hydroxy-$C_{1-6}$-alkyl, $C_{1-6}$-alkyloxy-$C_{1-6}$-alkyl, $C_{1-6}$-alkylthio-$C_{1-6}$-alkyl, $C_{1-6}$-fluoroalkyl or benzyl groups;

$R_{e1}$ represents an —$NR_4R_5$ group or a cyclic monoamine optionally comprising an oxygen atom, the cyclic monoamine being optionally substituted with one or more substituents chosen from a fluorine atom and $C_{1-6}$-alkyl, $C_{1-6}$-alkyloxy and hydroxyl groups;

two $R_{e2}$ groups form, with the carbon atom that bears them, a cyclic monoamine optionally comprising an oxygen atom, the cyclic monoamine being optionally substituted with one or more $R_f$ groups, which may be identical to or different from one another;

$R_f$ represents a $C_{1-6}$-alkyl, $C_{3-7}$-cycloalkyl, $C_{3-7}$-cycloalkyl-$C_{1-6}$-alkyl, $C_{1-6}$-alkyloxy-$C_{1-6}$-alkyl, hydroxy-$C_{1-6}$-alkyl, $C_{1-6}$-fluoroalkyl, phenyl or benzyl group;

$R_4$ and $R_5$ represent, independently of one another, a hydrogen atom or a $C_{1-6}$-alkyl, $C_{3-7}$-cycloalkyl or $C_{3-7}$-cycloalkyl-$C_{1-6}$-alkyl group; and $R_7$ and $R_8$ represent, independently of one another, a hydrogen atom or a $C_{1-6}$-alkyl group.

2. The compound according to claim 1, wherein:
$R_2$ represents a phenyl optionally substituted with one or more halogen atoms or $C_{1-6}$-alkyl or $C_{1-6}$-fluoroalkyl groups.

3. The compound according to claim 1, wherein:
$R_2$ represents a group chosen from $C_{1-6}$-alkyl, $C_{1-6}$-fluoroalkyl, $C_{3-7}$-cycloalkyl or $C_{3-7}$-cycloalkyl-$C_{1-6}$-alkyl groups.

4. The compound according to claim 1, wherein:
$R_7$ and $R_8$ represent, independently of each other, a hydrogen atom or a methyl group.

5. The compound according to claim 1, wherein:
A represents a $C_{1-7}$-alkylene group optionally substituted with one or two $R_a$ groups;
B represents a $C_{1-7}$-alkylene group optionally substituted with an $R_b$ group;
L represents a nitrogen atom optionally substituted with an $R_c$ or $R_d$ group;
the carbon atoms of A and of B being optionally substituted with one or more $R_f$ groups, which may be identical to or different from each other;
two $R_a$ groups may together form a $C_{1-6}$-alkylene group;
$R_a$ and $R_b$ may together form a bond or a $C_{1-6}$-alkylene group;
$R_a$ and $R_c$ may together form a bond or a $C_{1-6}$-alkylene group;
$R_b$ and $R_c$ may together form a bond or a $C_{1-6}$-alkylene group;
$R_d$ represents a group chosen from a hydrogen atom and $C_{1-6}$-alkyl, $C_{3-7}$-cycloalkyl, $C_{3-7}$-cycloalkyl-$C_{1-6}$-alkyl, hydroxy-$C_{1-6}$-alkyl, $C_{1-6}$-alkyloxy-$C_{1-6}$-alkyl, $C_{1-6}$-alkylthio-$C_{1-6}$-alkyl, $C_{1-6}$-fluoroalkyl or benzyl groups; and
$R_f$ represents a $C_{1-6}$-alkyl, $C_{3-7}$-cycloalkyl, $C_{3-7}$-cycloalkyl-$C_{1-6}$-alkyl, $C_{1-6}$-alkyloxy-$C_{1-6}$-alkyl, hydroxy-$C_{1-6}$-alkyl, $C_{1-6}$-fluoroalkyl or phenyl group.

6. The compound according to claim 1, wherein:
A represents a $C_{1-7}$-alkylene group optionally substituted with one or two $R_a$ groups;
B represents a $C_{1-7}$-alkylene group optionally substituted with an $R_b$ group;
L represents a carbon atom optionally substituted with two $R_{e2}$ groups;
the carbon atoms of A and of B being optionally substituted with one or more $R_f$ groups, which may be identical to or different from each other;
two $R_{e2}$ groups form, with the carbon atom that bears them, a cyclic monoamine optionally comprising an oxygen atom, this cyclic monoamine being optionally substituted with one or more $R_f$ groups, which may be identical to or different from one another; and
$R_f$ represents a $C_{1-6}$-alkyl group.

7. The compound according to claim 1, wherein:
A represents a $C_{1-7}$-alkylene group;
B represents a $C_{1-7}$-alkylene group;
L represents a carbon atom substituted with an $R_{e1}$ group and an $R_d$ group;
$R_d$ represents a hydrogen atom;

R$_{e1}$ represents an —NR$_4$R$_5$ group or a cyclic monoamine optionally comprising an oxygen atom, the cyclic monoamine being optionally substituted with one or more R$_f$ groups, which may be identical to or different from one another; and R$_f$ represents a C$_{1-6}$-alkyl, C$_{3-7}$-cycloalkyl or C$_{3-7}$-cycloalkyl-C$_{1-6}$-alkyl group.

8. The compound according to claim 1, wherein:
R$_2$ represents a methyl group;
the cyclic amine formed by —N-A-L-B— represents an (R)-3-methylpiperazin-1-yl, 3,3-dimethylpiperazin-1-yl, (cis)-3,5-dimethylpiperazin-1-yl, 4-isopropylpiperazin-1-yl or (cis)-5-methylhexahydropyrrolo[3,4-c]pyrrol-2(1H)-yl group; and
R$_7$ and R$_8$ represent a hydrogen atom.

9. The compound according to claim 1, wherein:
R$_2$ represents a 3-fluorophenyl or a 4-fluorophenyl group;
the cyclic amine formed by —N-A-L-B— represents an (R)-3-methylpiperazin-1-yl, 3,3-dimethylpiperazin-1-yl, (cis)-3,5-dimethylpiperazin-1-yl, 4-isopropylpiperazin-1-yl, 6,9-diazaspiro[4.5]dec-9-yl, 3-phenylpiperazin-1-yl, 4-benzylpiperazin-1-yl, 3-hydroxymethylpiperazin-1-yl, 4-(2-hydroxyethyl)piperazin-1-yl, (R)-4-(2-hydroxypropyl)-piperazin-1-yl, (S)-4-(2-hydroxypropyl)piperazin-1-yl, 4-(1-hydroxy-2-methylpropan-2-yl)-piperazin-1-yl, 4-(2-hydroxy-2-methylpropyl)piperazin-1-yl, 4-(3-hydroxy-3-methylbutyl)-piperazin-1-yl, (R)-3-phenylpiperazin-1-yl, (S)-3-phenylpiperazin-1-yl, 4-benzylpiperazin-1-yl, (cis)-5-methylhexahydropyrrolo[3,4-c]pyrrol-2(1H)-yl, (cis)-5-(2-hydroxyethyl)hexahydro-pyrrolo[3,4-c]pyrrol-2(1H)-yl, (4aR,7aR)-1-methyloctahydro-6H-pyrrolo[3,4-b]pyridin-6-yl, (4aS,7aS)-1-methyloctahydro-6H-pyrrolo[3,4-b]pyridin-6-yl, or (1S,4S)-5-methyl-2,5-diaza-bicyclo[2.2.1]hept-2-yl group; and
R$_7$ and R$_8$ represent, independently of each other, a hydrogen atom or a methyl group.

10. The compound according to claim 1, wherein:
R$_2$ represents a 4-fluorophenyl group;
the cyclic amine formed by —N-A-L-B— represents a 2,9-diazaspiro[5.5]undec-9-yl group; and
R$_7$ and R$_8$ represent a hydrogen atom.

11. The compound according to claim 1, wherein:
R$_2$ represents a 4-fluorophenyl group;
the cyclic amine formed by —N-A-L-B— represents a 4-(pyrrolidin-1-yl)-piperidin-1-yl group;
R$_7$ and R$_8$ represent a hydrogen atom.

12. The compound according to claim 1, chosen from:
1. 2-Methyl-6-[(R)-3-methylpiperazin-1-yl]-3-(1H-pyrrolo[2,3-b]pyridin-4-yl)imidazo[1,2-b]pyridazine;
2. 6-(3,3-Dimethylpiperazin-1-yl)-2-methyl-3-(1H-pyrrolo[2,3-b]pyridin-4-yl)imidazo[1,2-b]pyridazine and the trihydrochloride thereof;
3. 6-[(cis)-3,5-Dimethylpiperazin-1-yl]-2-methyl-3-(1H-pyrrolo[2,3-b]pyridin-4-yl)-imidazo[1,2-b]pyridazine and the trihydrochloride thereof;
4. 6-(4-Isopropylpiperazin-1-yl)-2-methyl-3-(1H-pyrrolo[2,3-b]pyridin-4-yl)imidazo[1,2-b]pyridazine and the trihydrochloride thereof;
5. 2-Methyl-6-[(cis)-5-methylhexahydropyrrolo[3,4-c]pyrrol-2(1H)-yl]-3-(1H-pyrrolo[2,3-b]pyridin-4-yl)imidazo[1,2-b]pyridazine and the trihydrochloride thereof;
6. 2-(4-Fluorophenyl)-6-[(3R)-3-methylpiperazin-1-yl]-3-(1H-pyrrolo[2,3-b]pyridin-4-yl)-imidazo[1,2-b]pyridazine;
7. {4-[2-(4-Fluorophenyl)-3-(1H-pyrrolo[2,3-b]pyridin-4-yl)imidazo[1,2-b]pyridazin-6-yl]-piperazin-2-yl}methanol;
8. 6-(3,3-Dimethylpiperazin-1-yl)-2-(4-fluorophenyl)-3-(1H-pyrrolo[2,3-b]pyridin-4-yl)-imidazo[1,2-b]pyridazine;
9. 6-(3,3-Dimethylpiperazin-1-yl)-2-(3-fluorophenyl)-8-methyl-3-(1H-pyrrolo[2,3-b]pyridin-4-yl)imidazo[1,2-b]pyridazine;
10. 6-(3,3-Dimethylpiperazin-1-yl)-2-(4-fluorophenyl)-8-methyl-3-(1H-pyrrolo[2,3-b]pyridin-4-yl)imidazo[1,2-b]pyridazine;
11. 6-[(cis)-3,5-Dimethylpiperazin-1-yl]-2-(4-fluorophenyl)-3-(1H-pyrrolo[2,3-b]pyridin-4-yl)imidazo[1,2-b]pyridazine;
12. 2-{4-[2-(3-Fluorophenyl)-8-methyl-3-(1H-pyrrolo[2,3-b]pyridin-4-yl)imidazo[1,2-b]pyridazin-6-yl]piperazin-1-yl}ethanol;
13. 2-{4-[2-(4-Fluorophenyl)-8-methyl-3-(1H-pyrrolo[2,3-b]pyridin-4-yl)imidazo[1,2-b]pyridazin-6-yl]piperazin-1-yl}ethanol;
14. 2-(4-Fluorophenyl)-6-(4-isopropylpiperazin-1-yl)-3-(1H-pyrrolo[2,3-b]pyridin-4-yl)-imidazo[1,2-b]pyridazine;
15. 2-(4-Fluorophenyl)-6-(4-isopropylpiperazin-1-yl)-8-methyl-3-(1H-pyrrolo[2,3-b]pyridin-4-yl)imidazo[1,2-b]pyridazine;
16. (R)-1-{4-[2-(4-Fluorophenyl)-8-methyl-3-(1H-pyrrolo[2,3-b]pyridin-4-yl)imidazo[1,2-b]pyridazin-6-yl]piperazin-1-yl}propan-2-ol;
17. (S)-1-{4-[2-(4-Fluorophenyl)-8-methyl-3-(1H-pyrrolo[2,3-b]pyridin-4-yl)imidazo[1,2-b]pyridazin-6-yl]piperazin-1-yl}propan-2-ol;
18. 6-(6,9-Diazaspiro[4.5]dec-9-yl)-2-(4-fluorophenyl)-8-methyl-3-(1H-pyrrolo[2,3-b]pyridin-4-yl)imidazo[1,2-b]pyridazine;
19. 2-{4-[2-(4-Fluorophenyl)-3-(1H-pyrrolo[2,3-b]pyridin-4-yl)imidazo[1,2-b]pyridazin-6-yl]piperazin-1-yl}-2-methylpropan-1-ol;
20. 1-{4-[2-(4-Fluorophenyl)-3-(1H-pyrrolo[2,3-b]pyridin-4-yl)imidazo[1,2-b]pyridazin-6-yl]piperazin-1-yl}-2-methylpropan-2-ol;
21. 1-{4-[2-(3-Fluorophenyl)-8-methyl-3-(1H-pyrrolo[2,3-b]pyridin-4-yl)imidazo[1,2-b]pyridazin-6-yl]piperazin-1-yl}-2-methylpropan-2-ol;
22. 1-{4-[2-(4-Fluorophenyl)-8-methyl-3-(1H-pyrrolo[2,3-b]pyridin-4-yl)imidazo[1,2-b]pyridazin-6-yl]piperazin-1-yl}-2-methylpropan-2-ol;
23. 4-{4-[2-(4-Fluorophenyl)-3-(1H-pyrrolo[2,3-b]pyridin-4-yl)imidazo[1,2-b]pyridazin-6-yl]piperazin-1-yl}-2-methylbutan-2-ol;
24. (R)-2-(4-Fluorophenyl)-6-[3-phenylpiperazin-1-yl]-3-(1H-pyrrolo[2,3-b]pyridin-4-yl)-imidazo[1,2-b]pyridazine and the trihydrochloride thereof;
25. (S)-2-(4-Fluorophenyl)-6-[3-phenylpiperazin-1-yl]-3-(1H-pyrrolo[2,3-b]pyridin-4-yl)-imidazo[1,2-b]pyridazine and the trihydrochloride thereof;
26. 2-(4-Fluorophenyl)-8-methyl-6-[3-phenylpiperazin-1-yl]-3-(1H-pyrrolo[2,3-b]pyridin-4-yl)imidazo[1,2-b]pyridazine;
27. 6-(4-Benzylpiperazin-1-yl)-2-(4-fluorophenyl)-3-(1H-pyrrolo[2,3-b]pyridin-4-yl)imidazo[1,2-b]pyridazine;
28. (cis)-2-(4-Fluorophenyl)-6-(5-methylhexahydropyrrolo[3,4-c]pyrrol-2(1H)-yl)-3-(1H-pyrrolo[2,3-b]pyridin-4-yl)imidazo[1,2-b]pyridazine;

29. (cis)-2-(4-Fluorophenyl)-8-methyl-6-(5-methyl-hexahydropyrrolo[3,4-c]pyrrol-2(1H)-yl)-3-(1H-pyrrolo[2,3-b]pyridin-4-yl)imidazo[1,2-b]pyridazine;

30. (cis)-2-{5-[2-(4-Fluorophenyl)-3-(1H-pyrrolo[2,3-b]pyridin-4-yl)imidazo[1,2-b]pyridazin-6-yl]hexahydropyrrolo[3,4-c]pyrrol-2(1H)-yl}ethanol;

31. (cis)-2-{5-[2-(4-Fluorophenyl)-8-methyl-3-(1H-pyrrolo[2,3-b]pyridin-4-yl)imidazo[1,2-b]pyridazin-6-yl]hexahydropyrrolo[3,4-c]pyrrol-2(1H)-yl}ethanol;

32. 2-(4-Fluorophenyl)-8-methyl-6-((4aR,7aR)-1-methyloctahydro-6H-pyrrolo[3,4-b]pyridin-6-yl)-3-(1H-pyrrolo[2,3-b]pyridin-4-yl)imidazo[1,2-b]pyridazine;

33. 2-(4-Fluorophenyl)-8-methyl-6-((4aS,7aS)-1-methyloctahydro-6H-pyrrolo[3,4-b]pyridin-6-yl)-3-(1H-pyrrolo[2,3-b]pyridin-4-yl)imidazo[1,2-b]pyridazine;

34. 2-(4-Fluorophenyl)-6-((1S,4S)-5-methyl-2,5-diazabicyclo[2.2.1]hept-2-yl)-3-(1H-pyrrolo[2,3-b]pyridin-4-yl)imidazo[1,2-b]pyridazine;

35. 9-[2-(4-Fluorophenyl)-3-(1H-pyrrolo[2,3-b]pyridin-4-yl)imidazo[1,2-b]pyridazin-6-yl]-2,9-diazaspiro[5.5]undecane;

36. 2-(4-Fluorophenyl)-6-(4-pyrrolidin-1-ylpiperidin-1-yl)-3-(1H-pyrrolo[2,3-b]pyridin-4-yl)imidazo[1,2-b]pyridazine.

13. A pharmaceutical composition comprising the compound according to claim 1, in the form of a base or an addition salt with a pharmaceutically acceptable acid.

14. The pharmaceutical composition according to claim 13 further comprising, at least one pharmaceutically acceptable excipient.

15. A process for preparing the compound according to claim 1, which comprises reacting a compound of general formula (II):

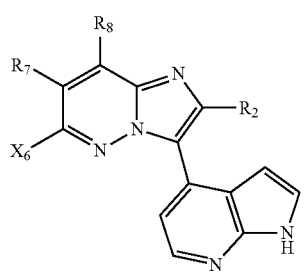

(II)

in which $R_2$, $R_7$ and $R_8$ are as defined according to claim 1 and $X_6$ represents a leaving group, with an amine of general formula (III):

(III)

in which A, L and B are as defined according to claim 1.

16. A process for preparing the compound according to claim 1, comprising deprotecting a compound of general formula (V):

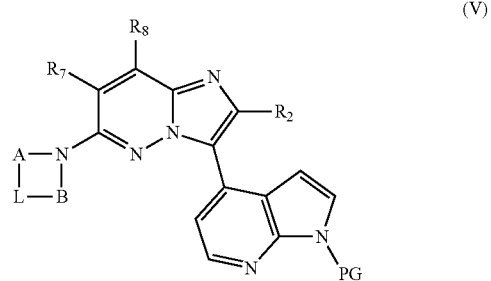

(V)

in which $R_2$, A, L, B, $R_7$ and $R_8$ are as defined according to claim 1 and PG represents a benzene or toluenesulphonyl group, using a base.

17. A method for inhibiting casein kinase I epsilon and/or casein kinase delta comprising adding a solution comprised of said casein kinase I epsilon or casein kinase delta a compound of the formula

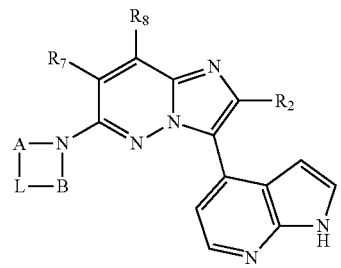

or in the form of a base or of an addition salt with an acid, in which:

$R_2$ represents an aryl group optionally substituted with one or more substituents chosen from halogen atoms and $C_{1-6}$-alkyl, $C_{1-6}$-alkyloxy, $C_{1-6}$-alkylthio, $C_{1-6}$-fluoroalkyl, $C_{1-6}$-fluoroalkyloxy and —CN groups or $R_2$ represents a $C_{1-6}$-alkyl, $C_{1-6}$-fluoroalkyl, $C_{3-7}$-cycloalkyl or $C_{3-7}$-cycloalkyl-$C_{1-6}$-alkyl group;

A represents a $C_{1-7}$-alkylene group optionally substituted with one or two $R_a$ groups;

B represents a $C_{1-7}$-alkylene group optionally substituted with an $R_b$ group;

L represents either a nitrogen atom optionally substituted with an $R_c$ or $R_d$ group, or a carbon atom substituted with an $R_{e1}$ group and an $R_d$ group or two $R_{e2}$ groups;

the carbon atoms of A and B being optionally substituted with one or more $R_f$ groups, which may be identical to or different from one another;

$R_a$, $R_b$ and $R_c$ are defined such that:
two $R_a$ groups may together form a $C_{1-6}$-alkylene group;
$R_a$ and $R_b$ may together form a bond or a $C_{1-6}$-alkylene group;
$R_a$ and $R_c$ may together form a bond or a $C_{1-6}$-alkylene group;
$R_b$ and $R_c$ may together form a bond or a $C_{1-6}$-alkylene group;

$R_d$ represents a group chosen from a hydrogen atom and $C_{1-6}$-alkyl, $C_{3-7}$-cycloalkyl, $C_{3-7}$-cycloalkyl-$C_{1-6}$-alkyl, hydroxy-$C_{1-6}$-alkyl, $C_{1-6}$-alkyloxy-$C_{1-6}$-alkylthio-$C_{1-6}$-alkyl, $C_{1-6}$-fluoroalkyl or benzyl groups;

$R_{e1}$ represents an —NR$_4$R$_5$ group or a cyclic monoamine optionally comprising an oxygen atom, the cyclic monoamine being optionally substituted with one or more substituents chosen from a fluorine atom and $C_{1-6}$-alkyl, $C_{1-6}$-alkyloxy and hydroxyl groups;

two $R_{e2}$ groups form, with the carbon atom that bears them, a cyclic monoamine optionally comprising an oxygen atom, the cyclic monoamine being optionally substituted with one or more $R_f$ groups, which may be identical to or different from one another;

$R_f$ represents a $C_{1-6}$-alkyl, $C_{3-7}$-cycloalkyl, $C_{1-6}$-alkyloxy-$C_{1-6}$-alkyl, hydroxy-$C_{1-6}$-alkyl, $C_{1-6}$-fluoroalkyl, phenyl or benzyl group;

$R_4$ and $R_5$ represent, independently of one another, a hydrogen atom or a $C_{1-6}$-alkyl, $C_{3-7}$-cycloalkyl or $C_{3-7}$-cycloalkyl-$C_{1-6}$-alkyl group; and $R_7$ and $R_8$ represent, independently of one another, a hydrogen atom or a $C_{1-6}$-alkyl group.

\* \* \* \* \*